United States Patent

Hansen et al.

Patent Number: 5,919,777
Date of Patent: Jul. 6, 1999

[54] COMPOUNDS WITH GROWTH HORMONE RELEASING PROPERTIES

[75] Inventors: Thomas Kruse Hansen, Herlev; Bernd Pesche, Måløv; Knud Erik Andersen, Smørum, all of Denmark

[73] Assignee: Novo Nordisk A/S, Bassvaerd, Denmark

[21] Appl. No.: 08/842,187

[22] Filed: Apr. 23, 1997

Related U.S. Application Data

[60] Provisional application No. 60/021,944, Jul. 17, 1996.

[30] Foreign Application Priority Data

Apr. 24, 1996 [DK] Denmark ................................ 0489/96
Nov. 26, 1996 [DK] Denmark ................................ 1344/96

[51] Int. Cl.$^6$ ................ C07D 241/08; C07D 241/04; C07D 401/12; A61K 31/495
[52] U.S. Cl. .................. 514/183; 514/212; 514/255; 540/481; 540/598; 544/363; 544/364; 544/365; 544/372; 544/374; 544/379; 544/382; 544/383; 544/384; 544/385; 544/386; 544/388; 544/389; 544/391; 544/396; 544/397; 544/399
[58] Field of Search ............................. 514/183, 212, 514/255; 540/481, 598; 544/363, 364, 365, 372, 374, 379, 382, 383, 384, 385, 386, 388, 389, 391, 396, 397, 399

[56] References Cited

U.S. PATENT DOCUMENTS 4,534,897  8/1985  Moon .................... 260/239.3
5,340,802  8/1994  Shiosaki et al. .................... 514/18
5,550,131  8/1996  Sugihara et al. .................... 514/255

FOREIGN PATENT DOCUMENTS

WO 95/17423  6/1995  WIPO .

OTHER PUBLICATIONS

Yamashita et al., "Structure–Activity Relationships of Dermorphin Analogues Containing Chiral Piperazin–2–one and Piperazine Derivatives", Chem. Pharm. Bull. vol. 44, No. 4, pp. 856–859 1996.

*Primary Examiner*—Mukund J. Shah
*Assistant Examiner*—Deepak R. Rao
*Attorney, Agent, or Firm*—Steve T. Zelson; Elias J. Lambiris; Carol E. Rozek

[57] ABSTRACT

The present invention relates to novel compounds of the general formula I

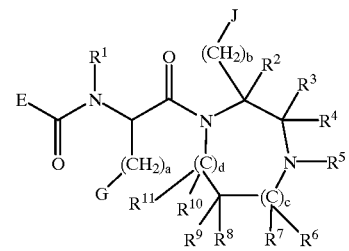

formula I which can be used for treating medical disorders resulting from a deficiency in growth hormone.

12 Claims, No Drawings

COMPOUNDS WITH GROWTH HORMONE RELEASING PROPERTIES

CROSS-REFERENCE TO RELATED APPLICATIONS

This application claims priority under 35 U.S.C. 119 from Danish application 0489/96 filed Apr. 24, 1996 and Danish application 1344/96 filed Nov. 26, 1996, and U.S. provisional application Ser. No. 60/021,944, filed Jul. 17, 1996, the contents of which applications are fully incorporated herein by reference.

FIELD OF INVENTION

The present invention relates to novel compounds, compositions containing them, and their use for treating medical disorders resulting from a deficiency in growth hormone.

BACKGROUND OF THE INVENTION

Growth hormone is a hormone which stimulates growth of all tissues capable of growing. In addition, growth hormone is known to have a number of effects on metabolic processes, e.g., stimulation of protein synthesis and free fatty acid mobilization and to cause a switch in energy metabolism from carbohydrate to fatty acid metabolism. Deficiency in growth hormone can result in a number of severe medical disorders, e.g., dwarfism.

Growth hormone is released from the pituitary. The release is under tight control of a number of hormones and neurotransmitters either directly or indirectly. Growth hormone release can be stimulated by growth hormone releasing hormone (GHRH) and inhibited by somatostatin. In both cases the hormones are released from the hypothalamus but their action is mediated primarily via specific receptors located in the pituitary. Other compounds which stimulate the release of growth hormone from the pituitary have also been described. For example arginine, L-3,4-dihydroxyphenylalanine (L-Dopa), glucagon, vasopressin, PACAP (pituitary adenylyl cyclase activating peptide), muscarinic receptor agonists and a synthethic hexapeptide, GHRP (growth hormone releasing peptide) release endogenous growth hormone either by a direct effect on the pituitary or by affecting the release of GHRH and/or somatostatin from the hypothalamus.

In disorders or conditions where increased levels of growth hormone is desired, the protein nature of growth hormone makes anything but parenteral administration non-viable. Furthermore, other directly acting natural secretagogues, e.g., GHRH and PACAP, are longer polypeptides for which reason oral administration of them is not viable.

The use of certain compounds for increasing the levels of growth hormone in mammals has previously been proposed, e.g. in EP 18 072, EP 83 864, WO 89/07110, WO 89/01711, WO 89/10933, WO 88/9780, WO 83/02272, WO 91/18016, WO 92/01711, WO 93/04081, WO 95/17422, WO 95/17423 and WO 95/14666.

The composition of growth hormone releasing compounds is important for their growth hormone releasing potency as well as their bioavailability. It is therefore an object of the present invention to provide novel compounds with growth hormone releasing properties which have improved properties relative to known compounds of this type.

SUMMARY OF THE INVENTION

In accordance with the present invention there is provided compounds which act directly on the pituitary cells under normal experimental conditions in vitro to release growth hormone therefrom.

These growth hormone releasing compounds can be utilized in vitro as unique research tools for understanding, inter alia, how growth hormone secretion is regulated at the pituitary level.

Moreover, the growth hormone releasing compounds of the present invention can also be administered in vivo to increase growth hormone release.

Accordingly, the present invention relates to a compound of general formula I formula I

[Chemical structure of formula I]

wherein $R^1$ is hydrogen, or $C_{1-6}$-alkyl optionally substituted with aryl;

a and b are independently 1 or 2;

c and d are independently 0, 1, or 2;

c+d is 0, 1, or 2;

$R^2$; $R^3$, $R^4$, $R^6$, $R^7$, $R^8$, $R^9$, $R^{10}$, and $R^{11}$ are independently hydrogen, aryl optionally substituted with halogen, amino, $C_{3-6}$-cycloalkyl, hydroxy, aryl, —$COOR^{22}$, or —$CONR^{23}R^{24}$, or $C_{1-6}$-alkyl optionally substituted with halogen, amino, $C_{3-6}$-cycloalkyl, hydroxy, aryl, —$COOR^{22}$, or —$CONR^{23}R^{24}$;

$R^3$ and $R^4$ can be taken together to form =O or =S;

$R^8$ and $R^9$ can be taken together to form =O or =S;

$R^5$ is hydrogen,

[Chemical structures showing various R⁵ substituents]

or $C_{1-6}$-alkyl optionally substituted with aryl, hydroxy, $C_{3-6}$-cycloalkyl, amino, —$COOR^{25}$, —$CONR^{26}R^{27}$, —$NR'R''$,

[Chemical structures showing NR ring substituents]

R, R' and R'' are independently hydrogen or $C_{1-6}$-alkyl;

$R^{30}$ and $R^{31}$ are independently $C_{1-6}$-alkyl optionally substituted with aryl, hydroxy, $C_{3-6}$-cycloalkyl, or amino;

$R^{22}$, $R^{23}$, $R^{24}$, $R^{25}$, $R^{26}$, and $R^{27}$ are independently hydrogen or $C_{1-6}$-alkyl; when $R^3$ and $R^4$ are taken together to form =O or =S, E is

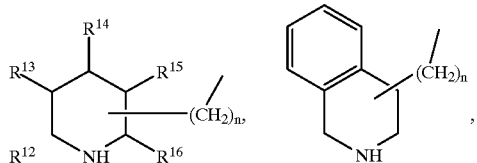

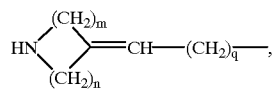

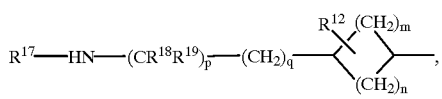

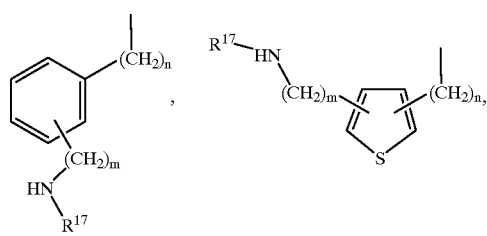

or $R^{17}NH$—$(CR^{18}R^{19})_p$—$(CH_2)_m$—M—$(CHR^{20})_o$—$(CH_2)_n$—;

when $R^3$ or $R^4$ is hydrogen, aryl optionally substituted with halogen, amino, $C_{3-6}$-cycloalkyl, hydroxy, aryl, —$COOR^{22}$, or —$CONR^{23}R^{24}$, or $C_{1-6}$-alkyl, optionally substituted with halogen, amino, $C_{3-6}$-cycloalkyl, hydroxy, aryl, —$COOR^{22}$, or —$CONR^{23}R^{24}$, E is

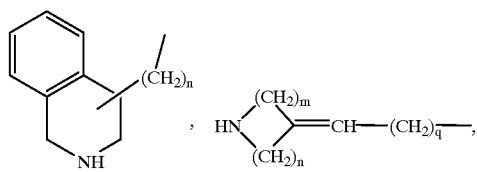

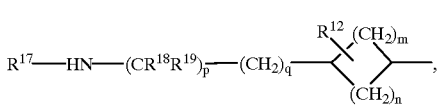

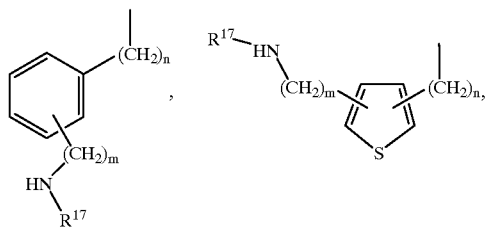

or $R^{17}NH$—$(CR^{18}R^{19})_p$—$(CH_2)_m$—Q—$(CHR^{20})_o$—$(CH_2)_n$—;

$R^{12}$, $R^{13}$, $R^{14}$, $R^{15}$, $R^{16}$, $R^{17}$, $R^{18}$, $R^{19}$, and $R^{20}$ are independently hydrogen or $C_{1-6}$-alkyl optionally substituted with halogen, amino, hydroxyl or aryl;

any two of $R^{17}$, $R^{18}$, and $R^{19}$ can independently be joined together to form an $C_{1-6}$-alkylene bridge;

n, m and q are independently 0, 1, 2, or 3;

o and p are independently 0 or 1;

M is —CH=$CR^{21}$—, —O——S—, or a valence bond;

Q is —CH=$CR^{21}$—, —O—, or —S—;

$R^{21}$ is hydrogen or $C_{1-6}$-alkyl optionally substituted with halogen, amino, hydroxyl or aryl;

G is hydrogen,

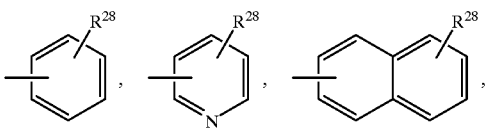

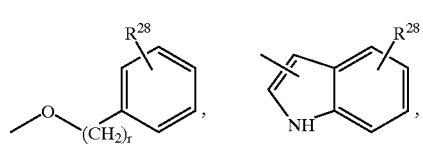

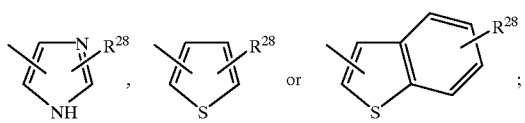

wherein $R^{28}$ is hydrogen, halogen, $C_{1-6}$-alkyl, $C_{1-6}$-alkoxy or aryl;

r is 0, 1, or 2;

J is hydrogen,

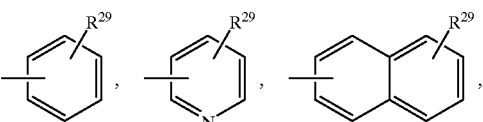

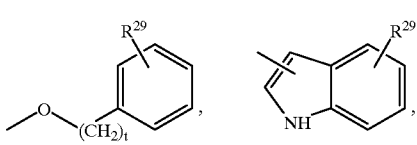

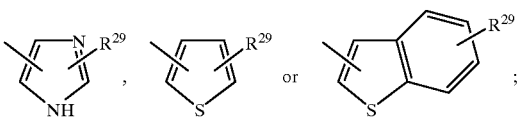

wherein $R^{29}$ is hydrogen, halogen, $C_{1-6}$-alkyl, $C_{1-6}$-alkoxy or aryl; t is 0, 1, or 2;

or a pharmaceutically acceptable salt thereof.

The compounds of formula I comprise any optical isomers thereof, in the form of separated, pure or partially purified optical isomers or racemic mixtures thereof.

The compounds of formula II–V are independently preferred embodiments of the compound of formula I, thus any reference in the present description to formula I also means reference to formula II–V.

In one embodiment of the compound of the above formula I $R^1$ is preferably $C_{1-6}$-alkyl, more preferred $C_{1-4}$-alkyl, such as methyl.

In a second embodiment of the compound of the above formula I a is preferably 1.

In a further embodiment of the compound of the above formula I b is preferably 1.

In a still further embodiment of the compound of the above formula I c is preferably 0 or 1.

In a further embodiment of the compound of the above formula I d is preferably 0 or 1.

In a still further embodiment of the compound of the above formula I c+d is preferably 1.

In a further embodiment of the compound of the above formula I $R^2$ is preferably hydrogen or $C_{1-4}$-alkyl, more preferred hydrogen.

In a still further embodiment of the compound of the above formula I $R^3$ and $R^4$ are preferably taken together to form =O or =S, more preferred =O.

In another embodiment of the compound of the above formula I $R^3$ and $R^4$ are independently of each other hydrogen.

In a further embodiment of the compound of the above formula I $R^5$ is preferably hydrogen, $C_{1-6}$-alkylsulfonyl, such as methylsulfonyl, or $C_{1-6}$-alkyl, more preferred $C_{1-4}$-alkyl, such as methyl.

In a still further embodiment of the compound of the above formula I $R^6$, $R^7$, $R^8$ and $R^9$ are independently of each other preferably hydrogen or $C_{1-6}$-alkyl, more preferred $C_{1-4}$-alkyl, such as methyl.

In a further embodiment of the compound of the above formula I $R^{10}$ and $R^{11}$ are independently of each other preferably hydrogen or $C_{1-4}$-alkyl, more preferred hydrogen.

In a still further embodiment of the compound of the above formula I E is preferably $$R^{17}NH-(CR^{18}R^{19})_p-(CH_2)_m-M-(CHR^{20})_o(CH_2)_n-,$$

wherein $R^{17}$ is hydrogen or $C_{1-4}$ alkyl, preferably methyl,
$R^{18}$ is hydrogen or $C_{1-4}$ alkyl, preferably methyl, and
$R^{19}$ is hydrogen or $C_{1-4}$ alkyl, preferably methyl, or
$R^{18}$ and $R^{19}$ are joined together to form a $C_{1-6}$-alkylene bridge, preferably a
$C_{1-4}$-alkylene bridge, such as a trimethylene-bridge, and
n is 0 or 1, preferably 0,
p is 1, m is 1 and M is —CH=$CR^{21}$, wherein $R^{21}$ is hydrogen or $C_{1-4}$ alkyl,
preferably methyl,
more preferred E is —CH=CH—$CH_2$—$C(CH_3)_2NH_2$, —CH=$C(CH_3)$—$CH_2$—$C(CH_3)_2NH_2$, —CH=CH—$CH_2$—$C(CH_3)_2$—$NH(CH_3)$ or

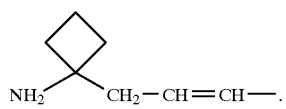

In a further embodiment of the compound of the above formula I G is preferably

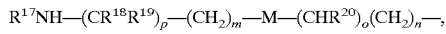

wherein $R^{28}$ is hydrogen or aryl, preferably phenyl, more preferred G is 2-naphthyl or biphenyl-4-yl.

In a still further embodiment of the compound of the above formula I J is preferably

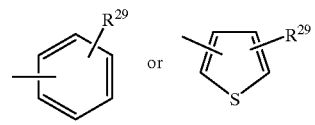

wherein $R^{29}$ is hydrogen or $C_{1-6}$-alkyl, preferably hydrogen, more preferred J is phenyl or 2-thienyl.

Preferred compounds of the invention are:

(2E)-5-Amino-5-methylhex-2-enoic acid N-((1R)-1-((2R)-2-benzyl-3-oxopiperazine-1-carbonyl)-2-(2-naphthyl)ethyl)-N-methylamide;

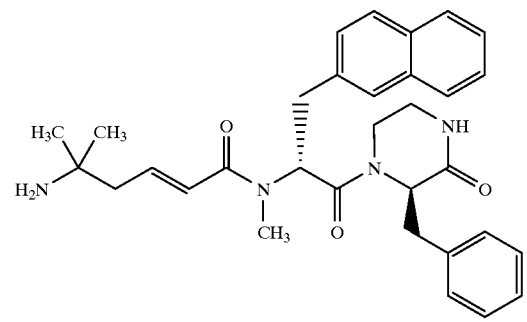

(2E)-5-Amino-5-methylhex-2-enoic acid N-((1R)-1-((2R)-2-benzyl-4-(cyclopropylmethyl)-3-oxopiperazine-1-carbonyl)-2-(2-naphthyl)ethyl)-N-methylamide:

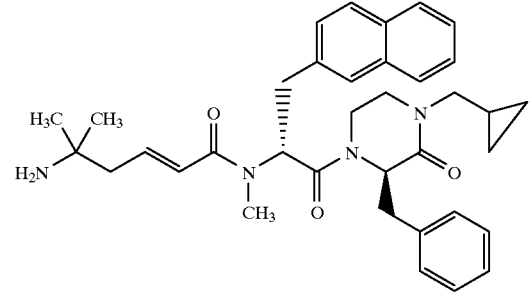

(2E)-5-Amino-5-methylhex-2-enoic acid N-((1R)-1-((2R,5R)-2-benzyl-5-(hydroxymethyl)3-oxopiperazine-1-carbonyl)-2-(2-naphthyl)ethyl)-N-methylamide:

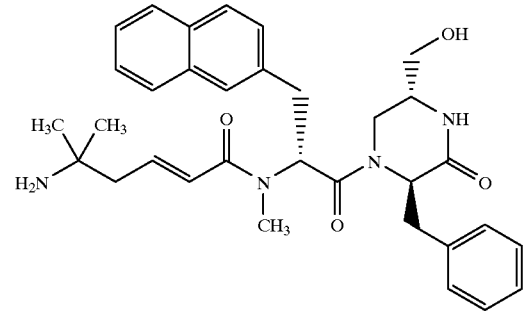

7

(2E)-5-Amino-5-methylhex-2-enoic acid N-((1R)-1-((2R)-2-benzyl-3-oxo-1,4-diaze-pane-1-carbonyl)-2-(2-naphthyl)ethyl)-N-methyl amide:

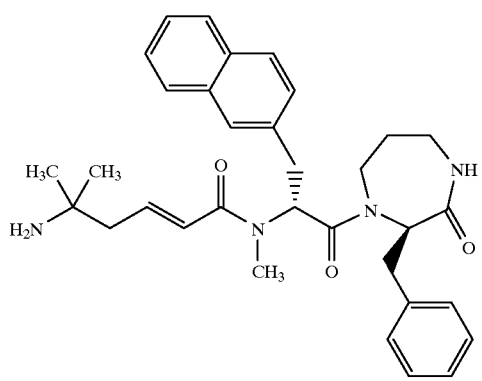

Piperidine-4-carboxylic acid N-methyl-N-((1R)-2-(2-napthyl)-1-((2R)-2-((2-napthyl)methyl)-3-oxopiperazine-1-carbonyl)ethyl) amide:

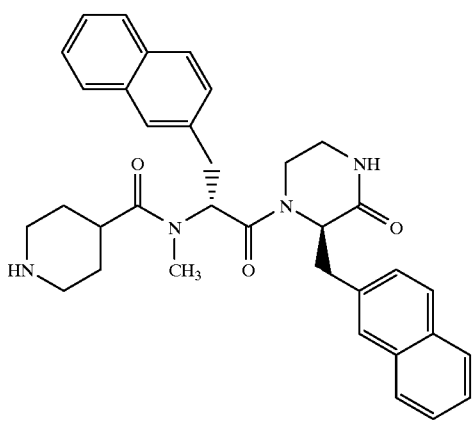

(2E)-5-Amino-5-methylhex-2-enoic acid N-((1R)-1-((2R)-2-benzyl-4-(dimethylcarbamoylmethyl)-3-oxopiperazine-1-carbonyl)-2-(2-naphthyl)ethyl)-N-methyl amide:

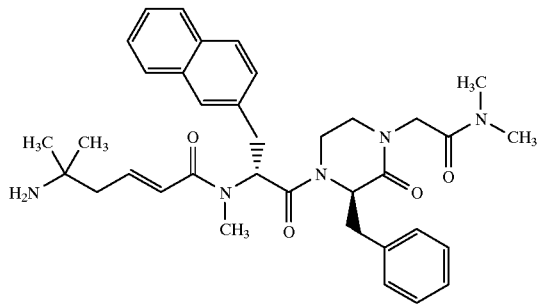

8

(2E)-5-Methyl-5-(methylamino)hex-2-enoic acid N-((1R)-1-((2R)-2-benzyl-3-oxo-piperazine-1-carbonyl)-2-(2-naphthyl)ethyl)-N-methylamide:

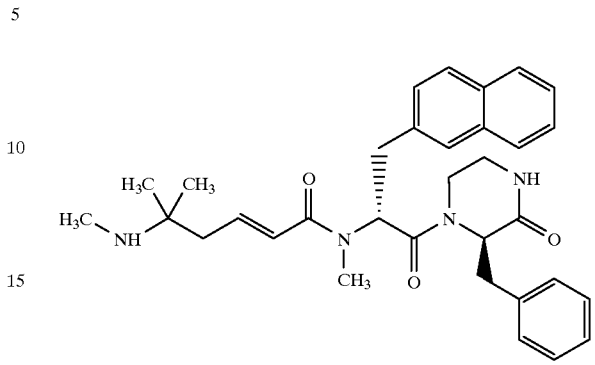

(2E)-5-Amino-5-methylhex-2-enoic acid N-((1R)-1-((2R,6S)-2-benzyl-6-methyl-3-oxopiperazine-1-carbonyl)-2-(2-naphthyl)ethyl)-N-methylamide:

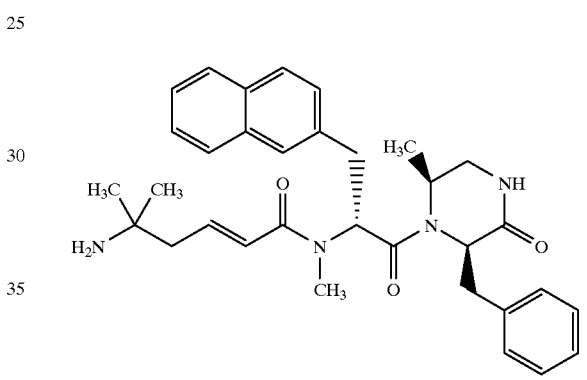

(2E)-5-Amino-5-methylhex-2-enoic acid N-((1R)-1-((2R)-2-benzyl-3-oxo-piperazine-1-carbonyl)-2-(biphenyl-4-yl)ethyl)-N-methylamide:

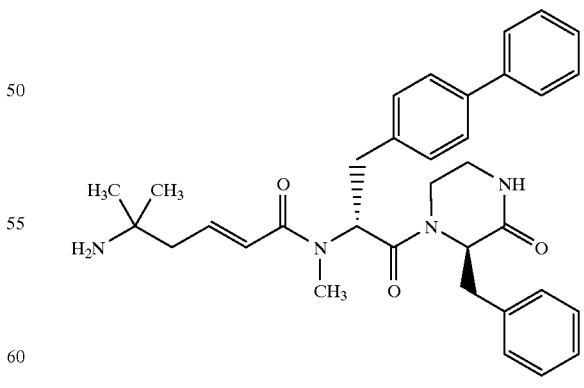

(2E)-5-Amino-5-methylhex-2-enoic acid N-((1R)-1-((2R)-2-benzyl-4-methanesulfonylpiperazine-1-carbonyl)-2-(2-naphthyl)ethyl)-N-methylamide:

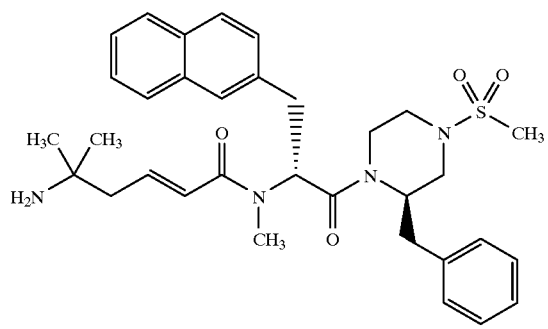

(2E)-5-Methyl-5-methylaminohex-2-enoic acid N-((1R)-1-((2R,5R)-2-benzyl-5-methyl-3-oxopiperazine-1-carbonyl)-2-(2-naphthyl)ethyl)-N-methlamide.

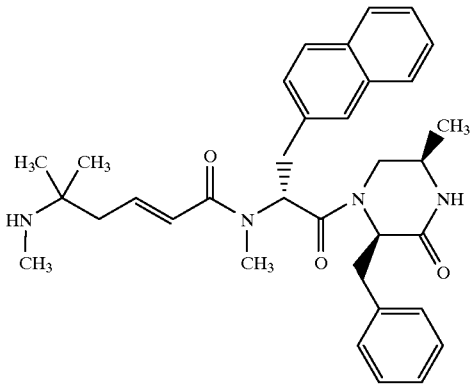

(2E)-5-Amino-5-methylhex-2-enoic acid N-((1R)-1-((2R)-2-benzyl-4-methanesulfonylpiperazine-1-carbonyl)-2-benzyloxyethyl)-N-methylamide:

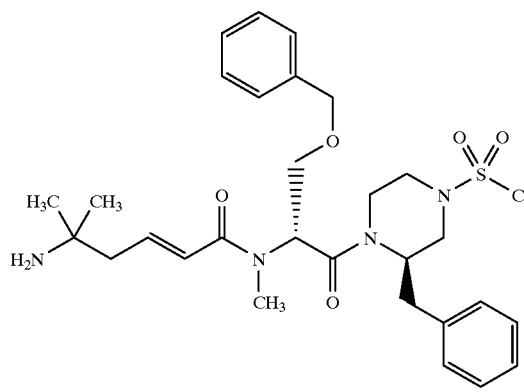

(2E)-5-Amino-5-methylhex-2-enoic acid N-((1R)-2-((2R)-2-benzyl-4-methyl-3-oxopiperazin-1-yl)-1-((2-naphthyl)methyl)-2-oxoethyl)-N-methylamide

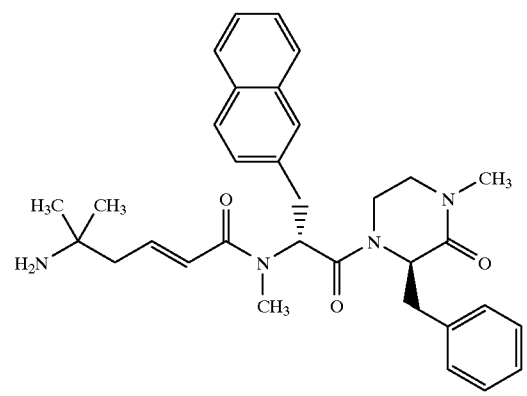

(2E)-5-Amino-3,5-dimethylhex-2-enoic acid N-((1R)-1-((2R)-2-benzyl-3-oxo-piperazine-1-carbonyl)-2-(2-naphthyl)ethyl)-N-methylamide.

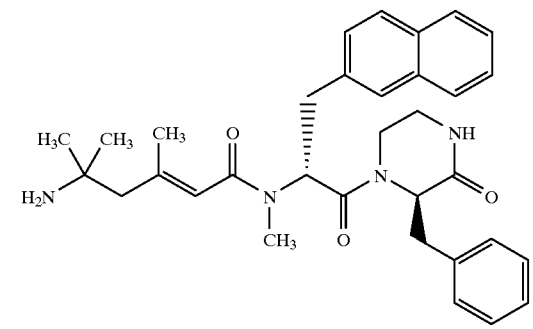

(2E)-5-Methyl-5-aminohex-2-enoic acid N-((1R)-1-((2R,5R)-2-benzyl-5-methyl-3-oxo piperazine-1-carbonyl)-2-(2-naphthyl)ethyl)-N-methylamide.

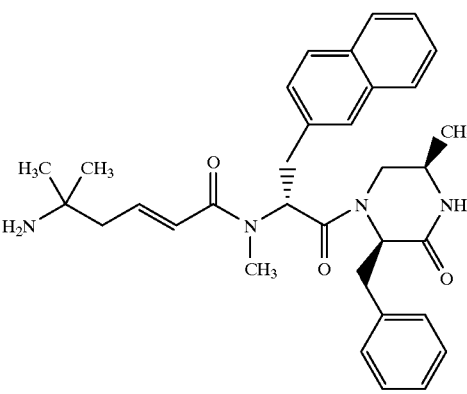

(2E)-4-(1-Aminocyclobutyl)but-2-enoic acid N-methyl-N-((1R)-2-(2-naphthyl)-1-((2R)-3-oxo-2-((2-thienyl)methyl)piperazine-1-carbonyl)ethyl)amide

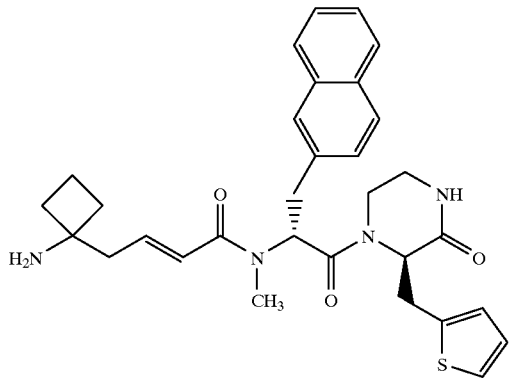

(2E)-4-(1-Aminocyclobutyl)but-2-enoic acid N-((1R)-2-((2R,5R)-2-benzyl-5-methyl-3-oxopiperazin-1-yl)-1-((2-naphthyl)methyl)-2-oxoethyl)-N-methylamide

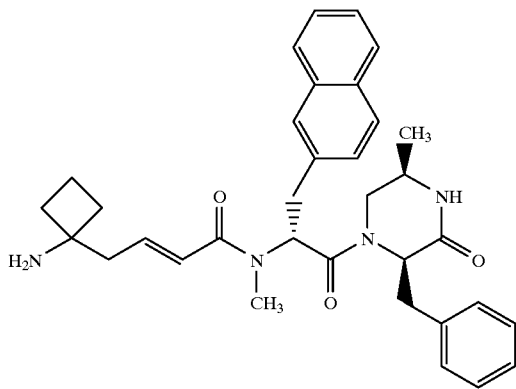

(2E) 5-Methyl-5-methylamino-hex-2-enoic acid N-methyl-N-((1R)-1-(2-naphthyl)methyl-2-oxo-2-((2R)-3-oxo-2-((2-thienyl)methyl)piperazin-1-yl)ethyl)amide.

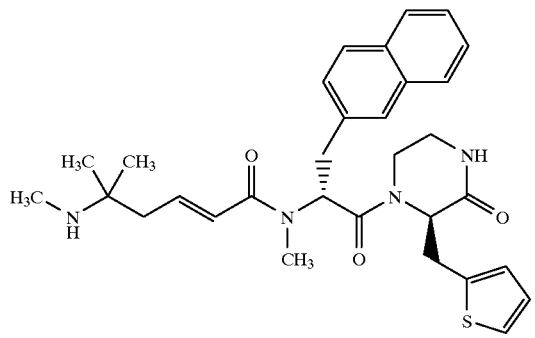

(2E)-5-Amino-5-methyl-hex-2-enoic acid (2-((2R)-2-benzyl-4-methanesulfonyl-piperazin-1-yl)-(1R)-1-(napht-2-ylmethyl)-2-oxo-ethyl)-methyl-amide.

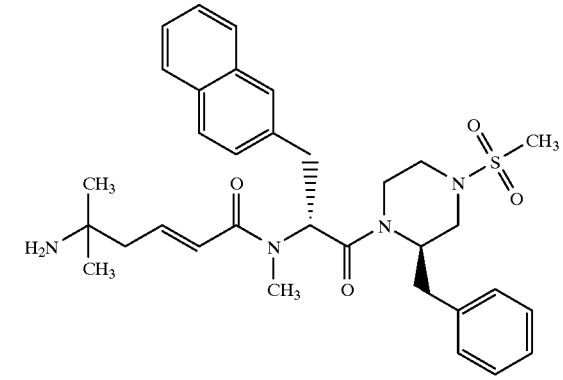

It is believed that compounds of formula I exhibit an improved resistance to proteolytic degradation by enzymes compared to that of the peptides suggested in the prior literature, due to the lack of natural peptide bonds. The increased resistance to proteolytic degradation combined with the reduced size of the compounds of the invention in comparison with known growth hormone releasing peptides is expected to improve their bioavailability compared to that of the peptides suggested in the prior literature.

In the above structural formulas and throughout the present specification, the following terms have the indicated meanings:

The $C_{1-6}$-alkyl, or $C_{1-4}$-alkyl groups specified above are intended to include those alkyl groups of the designated length in either a linear or branched or cyclic configuration. Examples of linear alkyl are methyl, ethyl, propyl, butyl, pentyl, and hexyl. Examples of branched alkyl are isopropyl, sec-butyl, tert-butyl, isopentyl, and isohexyl. Examples of cyclic alkyl are $C_{3-6}$-cycloalkyl such as cyclopropyl, cyclobutyl, cyclopentyl and cyclohexyl.

The $C_{1-6}$-alkoxy groups specified above are intended to include those alkoxy groups of the designated length in either a linear or branched or cyclic configuration. Examples of linear alkyloxy are methoxy, ethoxy, propoxy, butoxy, pentoxy, and hexoxy. Examples of branched alkoxy are isopropoxy, sec-butoxy, tert-butoxy, isopentoxy, and isohexoxy. Examples of cyclic alkoxy are cyclopropyloxy, cyclobutyloxy, cyclopentyloxy and cyclohexyloxy.

In the present context, the term "aryl" is intended to include aromatic rings, such as carbocyclic and heterocyclic aromatic rings selected from the group consisting of phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, oxadiazolyl, thiopheneyl, quinolinyl, pyrazinyl, or isothiazolyl, optionally substituted by one or more $C_{1-6}$-alkyl, $C_{1-6}$-alkoxy, halogen, amino or aryl. Aryl is preferably phenyl, thienyl, imidazolyl, oxadiazolyl, pyridyl, indolyl, quinolinyl or naphthyl optionally substituted with halogen, amino, hydroxy, $C_{1-6}$-alkyl or $C_{1-6}$-alkoxy.

The term "halogen" is intended to include chlorine (Cl), fluorine (F), bromine (Br) and iodine (I).

The compounds of the present invention may have one or more asymmetric centres and it is intended that stereoisomers, as separated, pure or partially purified stereoisomers or racemic mixtures thereof are included in the scope of the invention.

The compounds of the present invention may optionally be on a pharmaceutically acceptable salt form such as the pharmaceutically acceptable acid addition salts of compounds of formula I which include those prepared by reacting the compound of formula I with an inorganic or organic acid such as hydrochloric, hydrobromic, sulfuric, acetic, phosphoric, lactic, maleic, phthalic, citric, glutaric, gluconic, methanesulfonic, salicylic, succinic, tartaric, toluenesulfonic, trifluoracetic, sulfamic or fumaric acid.

The compounds of formula I may be administered in pharmaceutically acceptable acid addition salt form or, where appropriate, as a alkali metal or alkaline earth metal or lower alkylammonium salt. Such salt forms are believed to exhibit approximately the same order of activity as the free base forms.

In another aspect, the present invention relates to a pharmaceutical composition comprising, as an active ingredient, a compound of the general formula I or a pharmaceutically acceptable salt thereof together with a pharmaceutically acceptable carrier or diluent.

Pharmaceutical compositions containing a compound of the present invention may be prepared by conventional techniques, e.g. as described in *Remington's Pharmaceutical Sciences,* 1985 or in Remington: The Science and Practice of Pharmacy, 19th Edition (1995). The compositions may appear in conventional forms, for example capsules, tablets, aerosols, solutions, suspensions or topical applications.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water.

Similarly, the carrier or diluent may include any sustained release material known in the art, such as glyceryl monostearate or glyceryl distearate, alone or mixed with a wax.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

A typical tablet which may be prepared by conventional tabletting techniques may contain:

Core:

| | | |
|---|---|---|
| Active compound (as free compound or salt thereof) | 100 | mg |
| Colloidal silicon dioxide (Aerosil) | 1.5 | mg |
| Cellulose, microcryst. (Avicel) | 70 | mg |
| Modified cellulose gum (Ac-Di-Sol) | 7.5 | mg |
| Magnesium stearate | | |
| Coating: | | |
| HPMC approx. | 9 | mg |
| *Mywacett 9-40 T approx. | 0.9 | mg |

*Acylated monoglyceride used as plasticizer for film coating.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

Generally, the compounds of the present invention are dispensed in unit dosage form comprising 50–200 mg of active ingredient together with a pharmaceutically acceptable carrier per unit dosage.

The dosage of the compounds according to this invention is suitably 0.1–500 mg/day, e.g. from about 5 to about 50 mg, such as about 10 mg per dose, when administered to patients, e.g. humans, as a drug.

It has been demonstrated that compounds of the general formula I possess the ability to release endogenous growth hormone in vivo. The compounds may therefore be used in the treatment of conditions which require increased plasma growth hormone levels such as in growth hormone deficient humans or in elderly patients or livestock.

Thus, in a particular aspect, the present invention relates to a pharmaceutical composition for stimulating the release of growth hormone from the pituitary, the composition comprising, as an active ingredient, a compound of the general formula I or a pharmaceutically acceptable salt thereof together with a pharmaceutically acceptable carrier or diluent.

In a further aspect, the present invention relates to a method of stimulating the release of growth hormone from the pituitary, the method comprising administering to a subject in need thereof an effective amount of a compound of the general formula I or a pharmaceutically acceptable salt thereof.

In a still further aspect, the present invention relates to the use of a compound of the general formula I or a pharmaceutically acceptable salt thereof for the preparation of a medicament for stimulating the release of growth hormone from the pituitary. To those skilled in the art, it is well known that the current and potential uses of growth hormone in humans are varied and multitudinous. Thus, compounds of formula I can be administered for purposes stimulating release of growth hormone from the pituitary and would then have similar effects or uses as growth hormone itself. The uses of growth hormone may be summarized as follows: stimulation of growth hormone release in the elderly; prevention of catabolic side effects of glucocorticoids, prevention and treatment of osteoporosis, stimulation of the immune system, acceleration of wound healing, accelerating bone fracture repair, accelerating complicated fractures, e.g. disctraction osteogenesis, treatment of wasting secondary to fractures, treatment of growth retardation, treating renal failure or insufficiency resulting from growth retardation, treatment of cardiomyopathy, treatment of chronic liver disease, treatment of thrombocytopenia, treatment of Crohn's disease, treatment of short bowel syndrome, treatment of chronic obstructive pulmonary disease (COPD), treatment of complications associated with transplantation, treatment of physiological short stature including growth hormone deficient children and short stature associated with chronic illness, treatment of obesity and growth retardation associated with obesity, treating growth retardation associated with the Prader-Willi syndrome and Turner's syndrome; accelerating the recovery and reducing hospitalization of burn patients; treatment of intrauterine growth retardation, skeletal dysplasia, hypercortisolism and Cushing's syndrome; induction of pulsatile growth hormone release; replacement of growth hormone in stressed patients, treatment of osteochondrodysplasias, Noonan's syndrome, schizophrenia, depressions, Alzheimer's disease, delayed wound healing and psychosocial deprivation, treatment of pulmonary dysfunction and ventilator dependency, attenuation of protein catabolic responses after major surgery, reducing cachexia and protein loss due to chronic illness such as cancer or AIDS; treatment of hyperinsulinemia including nesidioblastosis, adjuvant treatment for ovulation induction; to stimulate thymic development and prevent the age-related decline of thymic function, treatment of immunosuppressed patients, improvement in muscle strength, mobility, maintenance of skin thickness, metabolic homeostasis, renal homeostasis in the frail elderly, stimulation of osteoblasts, bone remodelling and cartilage growth, stimulation of the immune system in companion animals and treatment of disorder of aging in companion animals, growth promoter in livestock and stimulation of wool growth in sheep.

For the above indications the dosage will vary depending on the compound of formula I employed, on the mode of administration and on the therapy desired. However, generally dosage levels between 0.0001 and 100 mg/kg body weight daily are administered to patients and animals to obtain effective release of endogenous growth hormone. Usually, dosage forms suitable for oral, nasal, pulmonal or transdermal administration comprise from about 0.0001 mg to about 100 mg, preferably from about 0.001 mg to about 50 mg of the compounds of formula I admixed with a pharmaceutically acceptable carrier or diluent.

Optionally, the pharmaceutical composition of the invention may comprise a compound of formula I combined with one or more compounds exhibiting a different activity, e.g., an antibiotic or other pharmacologically active material.

The route of administration may be any route which effectively transports the active compound to the appropriate or desired site of action, such as oral, nasal, pulmonary, transdermal or parenteral, the oral route being preferred.

Apart from the pharmaceutical use of the compounds of formula I, they may be useful in vitro tools for investigating the regulation of growth hormone release.

Compounds of formula I may also be useful in vivo tools for evaluating the growth hormone releasing capability of the pituitary. For example, serum samples taken before and after administration of these compounds to humans can be assayed for growth hormone. Comparison of the growth hormone in each serum sample would directly determine the ability of the patients pituitary to release growth hormone.

Compounds of formula I may be administered to commercially important animals to increase their rate and extent of growth, and to increase milk production.

A further use of growth hormone secretagogue compounds of formula I is in combination with other secretagogues such as GHRP (2 or 6), GHRH and its analogues, growth hormone and its analogues or somatomedins including IGF-1 and IGF-2.

Pharmacological Methods

Compounds of formula I may be evaluated in vitro for their efficacy and potency to release growth hormone in rat pituitary primary cultures.

The isolation of rat pituitary cells is a modification of O. Sartor et al., *Endocrinology* 116, 1985, pp. 952–957. Male albino Sprague-Dawley rats (250±25 grams) were purchased from Mollegaard, Lille Skensved, Denmark. The rats were housed in group cages (four animals/cage) and placed in rooms with 12 hour light cycle. The room temperature varied from 19–24° C. and the humidity from 30–60%.

The rats were decapitated and the pituitaries dissected. The neurointermediate lobes were removed and the remaining tissue was immediately placed in icecold isolation buffer (Gey's medium (Gibco 041-04030) supplemented with 0.25% D-glucose, 2% non-essential amino acids (Gibco 043-01140) and 1% bovine serum albumine (BSA) (Sigma A-4503)). The tissue was cut into small pieces and transferred to isolation buffer supplemented with 3.8 mg/ml of trypsin (Worthington #3707 TRL-3) and 330 μg/ml of DNase (Sigma D4527). This mixture was incubated at 70 rotations/min for 35 min at 37° C. in a 95/5% atmosphere of $O_2/CO_2$. The tissue was then washed three times in the above buffer. Using a standard pasteur pipette, the tissue was then aspirated into single cells. After dispersion, cells were filtered through a nylon filter (160 μm) to remove undigested tissue. The cell suspension was washed 3 times with isolation buffer supplemented with trypsin inhibitor (0.75 mg/ml, Worthington #2829) and finally resuspended in culture medium; DMEM (Gibco 041-01965) supplemented with 25 mM HEPES (Sigma H-3375), 4 mM glutamine (Gibco 043-05030H), 0.075% sodium bicarbonate (Sigma S-8875), 0.1% non-essential amino acid, 2.5% fetal calf serum (FCS, Gibco 011-06290), 3% horse serum (Gibco 034-06050), 10% fresh rat serum, 1 nM $T_3$ (Sigma T-2752) and 40 μg/l dexamethasone (Sigma D-4902) pH 7.3, to a density of $2\times10^5$ cells/ml. The cells were seeded into microtiter plates (Nunc, Denmark), 200 μl/well, and cultured for 3 days at 37° C. and 8% $CO_2$.

Compound testing

After culturing, the cells were washed twice with stimulation buffer (Hanks Balanced Salt Solution (Gibco 041-04020) supplemented with 1% BSA (Sigma A-4503), 0.25% D-glucose (Sigma G-5250) and 25 mM HEPES (Sigma H-3375) pH 7.3) and preincubated for 1 hour at 37° C. The buffer was exchanged with 90 μl stimulation buffer (37° C.). Ten μl test compound solution was added and the plates were incubated for 15 min at 37° C. and 5% $CO_2$. The medium was decanted and analyzed for GH content in an rGH SPA test system.

All compounds were tested in doses ranging from 10 pM to 100 μM. A dose-response relation was constructed using the Hill equation (FIG. P, Biosoft). The efficacy (maximal GH released, $E_{max}$) was expressed in % of the $E_{max}$ of GHRP-6. The potency ($EC_{50}$) was determined as the concentration inducing half maximal stimulation of the GH release.

Compounds of formula I may be evaluated for their metabolic stability.

Compounds were dissolved at a concentration of 1 μg/μl in water. 25 μl of this solution is added to 175 μl of the respective enzyme-solution (resulting in an enzyme:substrate ratio (w/w) of approximately 1:5). The solution is left at 37° C. overnight. 10 μl of the various degradation solutions is analyzed against a corresponding zero-sample using flow injection electrospray mass spectrometry (ESMS) with selected ion monitoring of the molecular ion. If the signal has decreased more than 20% compared to the zero-sample, the remainder of the solution is analyzed by HPLC and mass spectrometry in order to identify the extent and site(s) of degradation precisely.

Several standard peptides (ACTH 4–10, Angiotensin 1–14 and Glucagon) have been included in the stability tests in order to verify the ability of the various solutions to degrade peptides.

Standard peptides (angiotensin 1–14, ACTH 4–10 and glucagon) were purchased from Sigma, Mo., USA)

Enzymes (trypsin, chymotrypsin, elastase aminopeptidase M and carboxypeptidase Y and B) were all purchased from Boehringer Mannheim GmbH (Mannheim, Germany)

17

Pancreatic enzyme mix: trypsin, chymotrypsin and elastase in 100 mM ammoniumbicarbonate pH 8.0 (all concentrations 0.025 μg/μl).

Carboxypeptidase mix: carboxypeptidase Y and B in 50 mM ammoniumacetate pH 4.5 (all concentrations 0.025 μg/μl).

Aminopeptidase M solution: aminopeptidase M (0.025 μg/μl) in 100 mM ammoniumbicarbonate pH 8.0

Mass spectrometric analysis was performed using two different mass spectrometers. A Sciex API III triple quadrupole LC-MS instrument (Sciex instruments, Thornhill, Ontario) equipped with an electrospray ion-source and a Bio-Ion 20 time-of-flight Plasma Desorption instrument (Bio-Ion Nordic AB, Uppsala, Sweden).

Quantification of the compounds (before and after degradation) was done on the API III instrument using single ion monitoring of the molecular ion in question with flow injection of the analyte. The liquid flow (MeOH:water 1:1) of 100 μl/min was controlled by an ABI 140B HPLC unit (Perkin-Elmer Applied Biosystems Divisions, Foster City, Calif.). The instrument parameters were set to standard operation conditions, and SIM monitoring was performed using the most intense molecular ion (in most cases this corresponded to the doubly charged molecular ion).

Identification of degradation products furthermore involved the use of plasma desorption mass spectrometry (PDMS) with sample application on nitrocellulose coated targets and standard instrumental settings. The accuracy of the hereby determined masses is generally better than 0.1%.

Separation and isolation of degradation products was done using a HY-TACH C-18 reverse phase 4.6×105 mm HPLC column (Hewlett-Packard Company, Palo Alto, Calif.) with a standard acetonitril: TFA separation gradient. The HPLC system used was HP1090M (Hewlett-Packard Company, Palo Alto, Calif.).

| Peptide derivative | MW/SIM ion (amu) | Carboxy-peptidase mix | Pan. enzyme mix |
|---|---|---|---|
| Standards | | | |
| ACTH 4-10 | 1124.5/562.8 | + | - |
| Glucagon | 3483/871.8 | - | - |
| Insulin (B23-29) | 859.1/430.6 | | |
| Angiotensin 1-14 | 1760.1/881.0 | - | - |
| GHRP-2 | 817.4/409.6 | - | - |
| GHRP-6 | 872.6/437.4 | - | - |

+: Stable (less than 20% decrease in SIM signal after 24 h in degradation solution)
-: Unstable (more than 20% decrease in SIM signal after 24 h in degradation solution)

Any novel feature or combination of features described herein is considered essential to this invention.

Chemical Methods

Some compounds of formula I or intermediates may be synthesized by one of the reactions sequences shown. Other examples may require different synthetic approaches, depending of the type of compound. The specific synthesis of each example is therefore given in the description of each example.

18

Method A

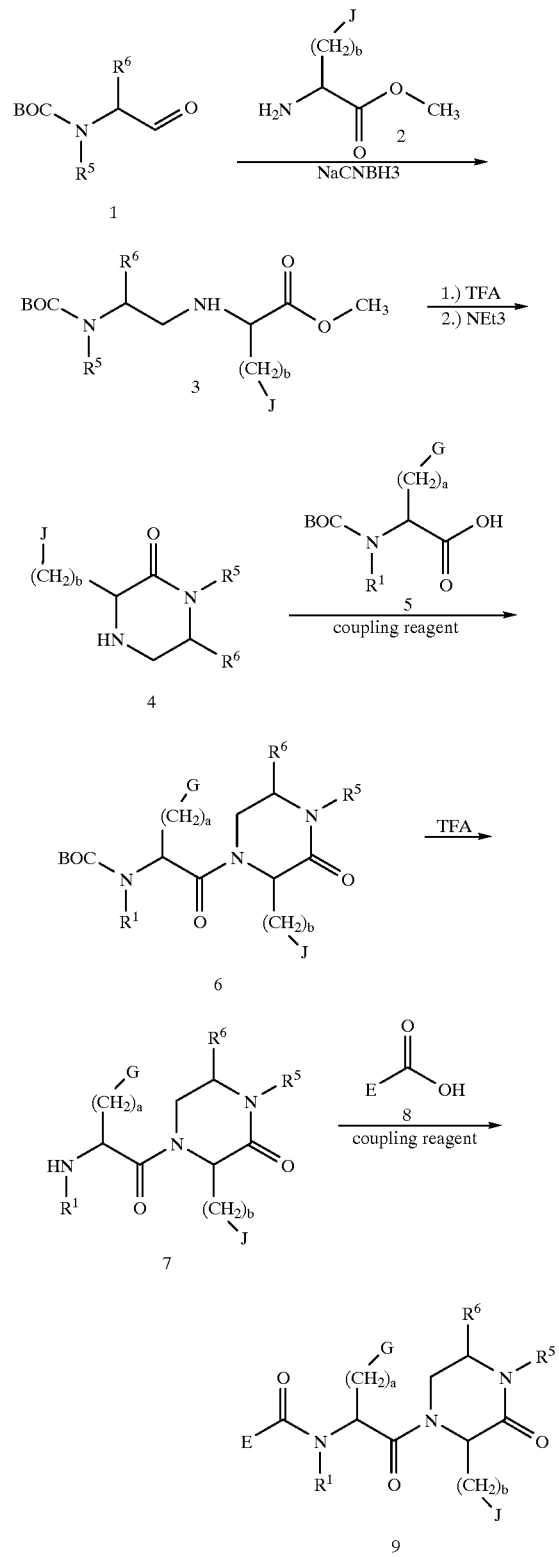

Scheme 1

An aldehyde 1 may be reacted with an ester 2 under reductive conditions such as e.g. sodium cyano borohydride to give an ester 3. After deprotection of the amino group a ring closure may take place to give a piperazinone 4. A reaction with a suitable protected amino acid 5 with a coupling reagent known in the art such as e.g. 1-ethyl-3-(3-dimethylaminopropyl)carbodiimide hydrochloride or a combination of 1-ethyl-3-(3-dimethylaminopropyl) carbodiimide hydrochloride and 1-hydroxybenzotriazole or 1-hydroxy-7-azabenzotriazole in an appropriate solvent such as e.g. N.N-dimethylformamide or dichloromethane may produce the piperazinone 6. After deprotection carried out with a method known in the art and described by e.g. T. W. Greene (Protective Groups in Organic Synthesis, 2. ed., John Wiley and Sons, New York 1991) e.g. trifluoroacetic acid or hydrogen chloride in ethyl acetate, the resulting amine 7 may be coupled with a suitable protected amino acid 8 with a coupling reagent known in the art such as e.g. 1-ethyl-3-(3-dimethylaminopropyl)carbodiimide hydrochloride or a combination of 1-ethyl-3-(3-dimethylaminopropyl)carbodiimide hydrochloride and 1-hydroxybenzotriazole or 1-hydroxy-7-azabenzotriazole in an appropriate solvent such as e.g. N,N-dimethylformamide or dichloromethane and successive deprotection with a method known in the art and described by e.g. T. W. Greene (Protective Groups in Organic Synthesis, 2. ed., John Wiley and Sons, New York 1991) e.g. trifluoroacetic acid or hydrogen chloride in ethyl acetate to give 9, which is a compound of formula I.

Method B

Scheme 2

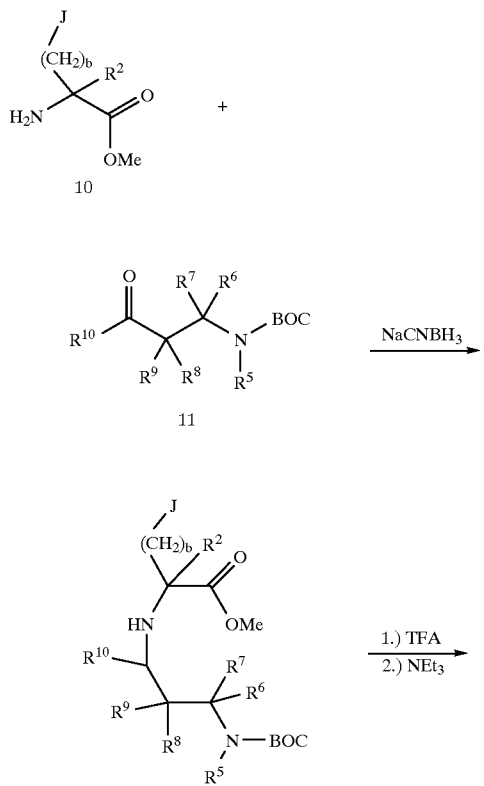

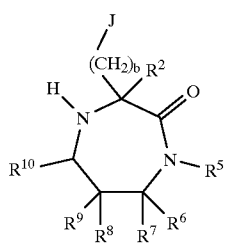

A diazepinone may be synthesized as described in scheme 2 and incorporated into the peptide in a similar fashion as in scheme 1 by reductive alkylation of a carbonyl-compound 11 onto an amino acid ester 10 under dehydrating conditions such as e.g. molecular sieves and sodium cyanoborohydride in a solvent such as e.g. methanol and subsequent removal of a protecting group from 12. This may result in cyclization of the intermediate to form 13. 13 may be used as an intermediate, which may be reacted in the same manner as described in scheme 1 for the intermediate 4 to give a compound of formula I.

EXAMPLES

The process for preparing compounds of formula I and preparations containing them is further illustrated in the following examples, which however, are not to be construed as limiting.

The structures of the compounds are confirmed by either elemental analysis (MA) nuclear magnetic resonance (NMR) or mass spectrometry (MS). NMR shifts ($\delta$) are given in parts per million (ppm) and only selected peaks are given. mp is melting point and is given in °C. Column chromatography was carried out using the technique described by W. C. Still et al, J. Org. Chem. 1978, 43, 2923–2925 on Merck silica gel 60 (Art 9385). Compounds used as starting materials are either known compounds or compounds which can readily be prepared by methods known per se.

Abbrevations

TLC: thin layer chromatography
DMSO: dimethylsulfoxide
min: minutes
h: hours

HPLC-Analysis

Method A1

The RP-analysis was performed using UV detections at 214, 254, 276, and 301 nm on a 218TP54 4.6 mm×250 mm 5 $\mu$ C-18 silica column (The Seperations Group, Hesperia), which was eluted at 1 mL/min at 42° C. The column was equilibrated with 5% acetonitrile in a buffer consisting of 0.1M ammonium sulfate, which was adjusted to pH 2.5 with 4M sulfuric acid after injection the sample was eluted by a gradient of 5% to 60% acetonitrile in the same buffer during 50 min.

Example 1

(2E)-5-Amino-5-methylhex-2-enoic acid N-((1R)-1-((2R)-2-benzyl-3-oxo-piperazin-1-carbonyl)-2-(2-naphthyl)ethyl)-N-methylamide.

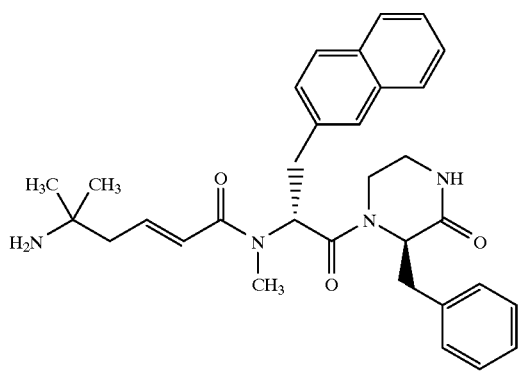

(2R)-2-(2-(tert-Butoxycarbonylamino)ethylamino)-3-phenylpropionic acid methyl ester.

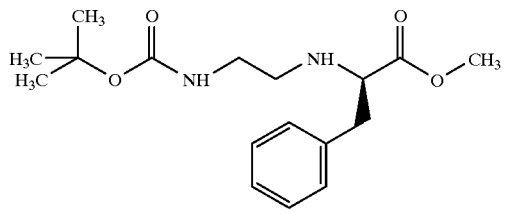

(2R)-2-Amino-3-phenylpropionic acid methyl ester (3.2 g; 15.0 mmol) and (2-oxoethyl)carbamic acid tert-butyl ester (3.2 g; 20.0 mmol) (prepared as in Dueholm et al, Org. Prep. Proced. Int. 25(4), 457–61 (1993)) were dissolved in a mixture of methanol (100 ml) and acetic acid (5 ml). Molecular sieves (3 Å; 100 g) were added and the reaction mixture was cooled to 0° C. Sodium cyanoborohydride (1.38 g; 22.0 mmol) was added portionwise and the reaction mixture was left without stirring for 12 h. The reaction mixture was filtered and water (100 ml), aqueous sodium hydrogencarbonate/sodium carbonate (10%; 100 ml; pH 9) and methylene chloride (50 ml) were added to the filtrate. The aqueous phase was extracted with methylene chloride (2×50 ml) and the combined organic phases were dried over magnesium sulfate. The organic phase was evaporated in vacuo and the residue was chromatographed on silica (4×40 cm) using ethyl acetate/heptane (3:2) as eluent to afford 2.07 g of (2R)-2-(2-(tert-butoxycarbonylamino)ethylamino)-3-phenylpropionic acid methyl ester.

$^1$H-NMR (CDCl$_3$): δ1.44 (s, 9H); 2.55 (m, 1H); 2.72 (m, 1H); 2.90 (dd, 1H); 2.97 (dd, 1H); 3.11 (m, 2H); 3.47 (t, 1H); 3.68 (s, 3H); 7.15–7.32 (arom., 5H);

(2R)-2-(2-Aminoethylamino)-3-phenylpropionic acid methyl ester.

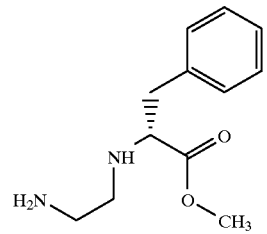

(2R)-2-(2-(tert-Butoxycarbonylamino)ethylamino)-3-phenylpropionic acid methyl ester (1.32 g; 4.094 mmol) was dissolved in methylene chloride (10 ml) and trifluoroacetic acid (10 ml) was added. The reaction mixture was stirred for 1 hour at room temperature. The solvent was evaporated in vacuo and the residue was dissolved in methylene chloride (5 ml) and evaporated in vacuo. Methylene chloride (5 ml) was added and evaporated in vacuo to afford 1.14 g of (2R)-2-(2-aminoethylamino)-3-phenylpropionic acid methyl ester as a trifluoroacetate salt.

$^1$H-NMR (DMSO-d$_6$): δ3.03–3.39 (m, 6H); 3.66 (s, 3H); 4.45 (dd, 1H); 7.21–7.39 (arom., 5H)

(3R)-3-Benzylpiperazin-2-one.

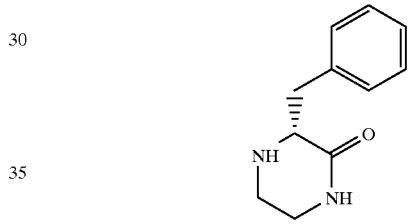

(2R)-2-(2-Aminoethylamino)-3-phenylpropionic acid methyl ester (0.67 g; 1.49 mmol) and triethylamine (1 ml) were dissolved in methylene chloride (10 ml) and stirred for 48 hours at room temperature. The reaction mixture was evaporated and the residue was chromatographed on silica (2.5×30 cm) using a 7% solution of ammonia in ethanol/methylene chloride (1:9) as eluent to afford 0.18 g of (3R)-3-benzylpiperazin-2-one.

$^1$H-NMR (CDCl$_3$): δ1.72 (s,br), 1H); 2.81–3.48 (m, 6H); 3.62 (dd, 1H); 6.92 (s(br), 1H); 7.19–7.36 (arom., 5H).

N-((1R)-2-((2R)-2-Benzyl-3-oxopiperazin-1-yl)-1-((2-naphthyl)methyl)-2-oxoethyl)-N-methylcarbamic acid tert-butyl ester.

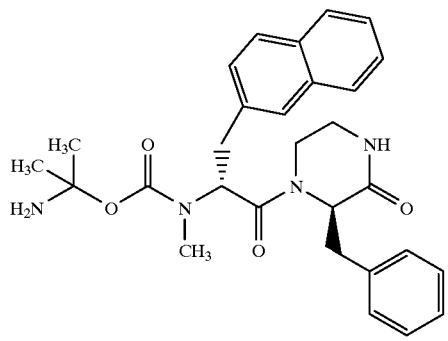

(2R)-2-(tert-Butoxycarbonylmethylamino)-3-(2-naphthyl)propionic acid (prepared as in J. R. Coggins, N. L. Benoitory, Can.J.Chem 49, 1968 (1971)) (0.327 g; 0.995 mmol) was dissolved in methylene chloride (10 ml). 1-Hydroxy-7-azabenzotriazole (0.135 g; 0.995 mmol) and N-(3-dimethylaminopropyl)-N'-ethylcarbodiimide hydrochloride (0.199 g; 1.042 mmol) were added and the reaction mixture was stirred for 10 min at room temperature. (3R)-3-Benzylpiperazin-2-one (0.180 g; 0.947 mmol) and diisopropylethylamine (0.134 g; 1.042 mmol) were added and the reaction mixture was stirred for 12 hours at room temperature. The reaction mixture was washed with 10% sodium hydrogensulfate (20 ml), saturated sodium hydrogencarbonate (20 ml), dried over magnesium sulfate and evaporated in vacuo. The residue was chromatographed on silica (2.5×25 cm) using ethyl acetate as eluent to afford 0.405 g of N-((1R)-2-((2R)-2-benzyl-3-oxopiperazin-1-yl)-1-((2-naphthyl)methyl)-2-oxoethyl)-N-methylcarbamic acid tert-butyl ester.

$^1$H-NMR (CDCl3): δ1.12, 1.25, 1.38 (three s, 9H); 2.54, 2,55, 2.78 (three s, 3H); 4.07, 4.42, 4.65, 4.79, 5.01, 5.30 (six m; 2H); 7.10–7.78 (arom., 12H) (mixture of rotamers, selected peaks).

(3R)-3-Benzyl4-((2R)-2-methylamino-3-(2-naphthyl)propionyl)piperazin-2-one.

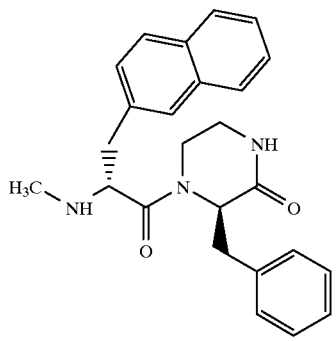

N-((1R)-2-((2R)-2-Benzyl-3-oxopiperazin-1-yl)-1-((2-naphthyl)methyl)- 2-oxoethyl)-N-methylcarbamic acid tert-butyl ester (0.405 g; 0.808 mmol) was dissolved in methylene chloride (5 ml) and trifluoroacetic acid (5 ml) and stirred 10 min at room temperature. Water (10 ml) and sodium hydrogencarbonate were added to pH 8. The reaction mixture was extracted with methylene chloride (2×30 ml), dried over magnesium sulfate and evaporated in vacuo to afford 0.302 g of (3R)-3-benzyl-4-((2R)-2-methylamino-3-(2-naphthyl)propionyl)piperazin-2-one.

$^1$H-NMR (CDCl$_3$): δ2.19, 2.28 (two s, 3H); 3.72, 4.66 (two dd, 1H); 4.96, 5.32 (two dd, 1H) (mixture of rotamers, selected peaks).

3-Hydroxy-1,1-dimethylpropylcarbamic acid tert-butyl ester.

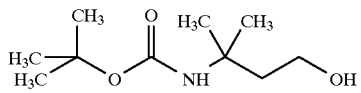

At 0° C., ethyl chloroformate (1.10 ml, 11.5 mmol) was given dropwise to a solution of 3-tert-butoxycarbonylamino-3-methylbutanoic acid (2.50 g, 11.5 mmol) (cf. Schoen et al. J. Med. Chem., 1994, vol. 37, p. 897–906, and references cited herein) and triethylamine (1.92 ml, 13.8 mmol) in tetrahydrofuran (10 ml). The solution was stirred for 40 min at 0° C. The formed precipitate was filtered off and washed with tetrahydrofuran (20 ml). The liquid was immediately cooled to 0° C. A 2M solution of lithium borohydride in tetrahydrofuran (14.4 ml, 28.8 mmol) was added dropwise. The solution was stirred at 0° C. for 2 h, and then warmed to room temperature over a period of 4 h. It was cooled to 0° C. and methanol (5 ml) was added. 1N Hydrochloric acid (100 ml) was added and the solution was extracted with ethyl acetate (2×100 ml, 3×50 ml). The combined organic extracts were washed with saturated sodium hydrogencarbonate solution (100 ml) and dried over magnesium sulfate. The solvent was removed in vacuo. The crude product was chromatographed on silica (110 g) with ethyl aceteate/heptane (1:2) to give 1.84 g of 3-hydroxy-1,1dimethylpropylcarbamic acid tert-butyl ester.

$^1$H-NMR (CDCl$_3$): δ1.33 (s, 6H); 1.44 (s, 9H); 1.88 (t, 2H); 1.94 (br, 1H); 3.75 (q,2H; 4.98 (br, 1H).

3-(tert-Butoxycarbonylaminomethyl)-3-methylbutanal.

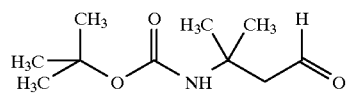

At −78° C. dimethylsulfoxide (1.22 ml, 17.2 mmol) was added to a solution of oxalyl chloride (1.1 ml, 12.9 mmol) in dichloromethane (15 ml). The mixture was stirred for 15 min at −78° C. A solution of 3-hydroxy-1,1-dimethylpropylcarbamic acid tert-butyl ester (1.75 g, 8.6 mmol) in dichloromethane (10 ml) was added dropwise over a period of 15 min. The solution was stirred at −78° C. for another 15 min.

Triethylamine (6.0 ml, 43 mmol) was added. The solution was stirred at −78° C. for 5 min and then warmed to room temperature. The solution was diluted with dichloromethane, (100 ml) and extracted with 1N hydrochloric acid (100 ml). The aqueous phase was extracted with dichloromethane (50 ml). The combined organic layers were washed with saturated sodium hydrogencarbonate solution (100 ml) and dried over magnesium sulfate. The solvent was removed in vacuo. The crude product was purified by column chromatography on silica (140 g) with ethyl acetate/heptane (1:3) to give 1.10 g of 3-(tert-butoxycarbonylaminomethyl)-3-methylbutanal.

$^1$H-NMR (CDCl$_3$): δ1.39 (s, 6H); 1.45 (s, 9H); 2.85 (d, 2H); 4.73 (br. 1H); 9.80 (t, 1H).

Ethyl (2E)-5-(tert-butoxycarbonylamino)-5-methylhex-2-enoate.

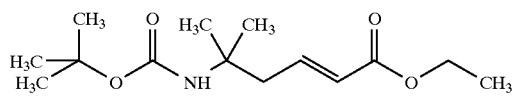

Triethylphosphonoacetate (1.96 ml, 9.8 mmol) was dissolved in tetrahydrofuran (30 ml). Potassium tert-butoxide (1.10 g, 9.8 mmol) was added. The solution was stirred for 40 min. at room temperature. A solution of 3-(tert-butoxycarbonyl-aminomethyl)-3-methylbutanal (1.10 g, 5.5 mmol) in tetrahydrofuran (6 ml) was added slowly. The solution was stirred at room temperature for 75 min. It was diluted with ethyl acetate (100 ml) and 1N hydrochloric acid (100 ml). The phases were separated. The aqueous phase was extracted with ethyl acetate (2×50 ml). The combined organic layers were washed with saturated sodium hydrogencarbonate solution (60 ml) and dried over magnesium sulfate. The solvent was removed in vacuo. The crude product was purified by column chromatography on silica (90 g) with ethyl acetate/heptane (1:4) to give 1.27 g of ethyl (2E)-5-(tert-butoxycarbonylamino)-5-methylhex-2-enoate.

$^1$H-NMR (CDCl$_3$): δ1.30 (s, 6H); 1.30 (t, 3H); 1.46 (s, 9H); 2.62 (d, 2H); 4.27 (q, 2H); 4.42 (br, 1H); 5.88 (d, 1H); 6.94 (td, 1H).

(2E)-5-(tert-Butyloxycarbonylamino)-5-methylhex-2-enoic acid.

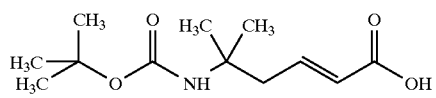

Ethyl (2E)-5-(tert-butoxycarbonylamino)-5-methylhex-2-enoate (1.23 g, 4.54 mmol) was dissolved in dioxane (20 ml). Lithium hydroxide (0.12 g, 5.00 mmol) was added as a solid. Water (10 ml) was added, until a clear solution was obtained. The solution was stirred for 16 h at room temperature. The solution was diluted with water (70 ml) and was extracted with tert-butyl methyl ether (2×100 ml). The aqueous phase was acidified with 1N sodium hydrogensulfate solution (pH 1) and extracted with tert-butyl methyl ether (3×70 ml). These organic layers were combined and dried over magnesium sulfate. The solvent was removed in vacuo to give 1.05 g of (2E)-5-(tert-butyloxycarbonylamino)-5-methylhex-2-enoic acid. The crude product was used for further syntheses.

$^1$H-NMR (DMSO-d$_6$): δ1.15 (s, 6H); 1.35 (s, 9H); 2.53 (d, 2H); 5.75 (d, 1H); 6.57 (br, 1H); 6.75 (td, 1H); 12.15 (s, 1H).

((3 E)-4-(N-((1R)-2-((2R)-2-Benzyl-3-oxopiperazin-1-yl)-1-((2-naphthyl)methyl-2-oxoethyl)-N-methylcarbamoyl)-1,1-dimethylbut-3-enyl)carbamic acid tert-butyl ester.

(2E)-5-(tert-Butyloxycarbonylamino)-5-methylhex-2-enoic acid (0.145 g; 0.599 mmol) was dissolved in methylene chloride. 1-Hydroxy-7-azabenzotriazole (0.081 g; 0.599 mmol) and N-(3-dimethylaminopropyl)-N'-ethylcarbodiimide hydrochloride (0.126 g; 0.658 mmol) were added and the reaction mixture was stirred for 15 min. (3R)-3-Benzyl-4-((2R)-2-methylamino-3-(2-naphthyl) propionylpiperazin-2-one (0.24 g; 0.599 mmol) and diisopropylethylamine (0.077 g; 0.599 mmol) were added and the reaction mixture was stirred for 12 hours at room temperature. The reaction mixture was washed with sodium hydrogensulfate (100 ml) and sodium hydrogencarbonate (100 ml). The organic phase was evaporated in vacuo and the residue was chromatographed on silica (2.5×20 cm) using ethyl acetate as eluent to afford 0.332 g of ((3E)-4-(N-((1R)-2-((2R)-2-benzyl-3-oxopiperazin-1-yl)-1-((2-naphthyl)-methyl)-2-oxoethyl)-N-methylcarbamoyl)-1,1-dimethylbut-3-enyl)carbamic acid tert-butyl ester.

$^1$H-NMR (CDCl$_3$): ) (mixture of rotamers, selected peaks for major rotamer) δ1.24 (s, 3H); 1.27 (s, 3H); 1.42 (s, 9H); 2.72 (s, 3H); 5.30 (dd, 1H); 5.81 (dd, 1H); 6.18 (d, 1H); 6.82 (m, 1H).

((3 E)-4-(N-((2R)-2-((2R)-2-benzyl-3-oxopiperazin-1-yl)-1-((2-naphthyl)methyl)-2-oxo-ethyl)-N-methylcarbamoyl)-1,1-dimethylbut-3-enyl)carbamic acid tert-butyl ester (0.32 g; 0.511 mmol) was dissolved in methylene chloride (4 ml) and trifluoroacetic acid (4 ml) was added. The reaction mixture was stirred 12 min at room temperature. Methylene chloride (50 ml) and water (50 ml) were added. Sodium hydrogencarbonate was added until pH 8. The organic phase was dried over magnesium sulfate and evaporated in vacuo to afford 0.232 g of the title compound.

$^1$H-NMR (CDCl$_3$): δ1.14, 1.15, 1.22,1.23 (four s, 6H); 4.05, 4.60,4.76, 5.12, 5.38, 5.81 (six dd, 2H); 6.18, 6.22 (d, 1H); 6.70, 6.81 (two m, 1H) (mixture of rotamers, selected peaks).

ESMS: m/z 527 (M+H)$^+$

HPLC (A1): r$_t$: 31.03 min.

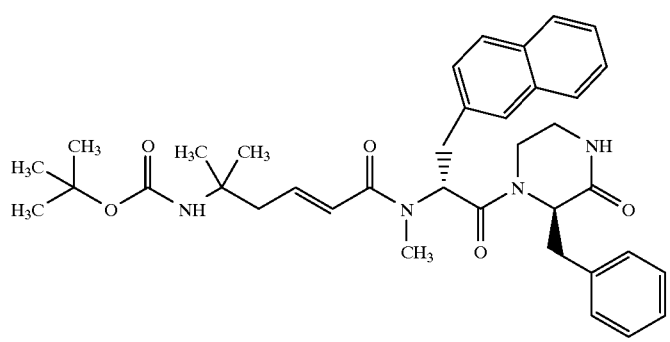

Example 2

(2E)-5-Amino-3,5-dimethylhex-2-enoic acid N-((1R)-1-((2R)-2-benzyl-3-oxopiperazine-1-carbonyl)-2-(2-naphthyl)ethyl)-N-methylamide.

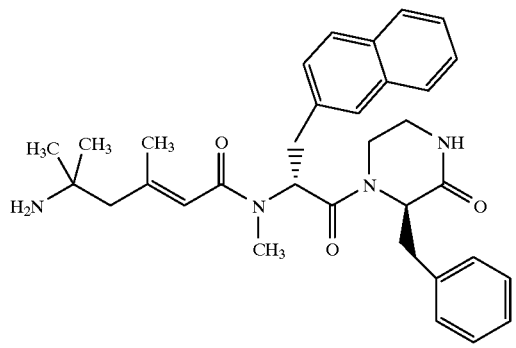

(1,1-Dimethyl-3-oxobutyl)carbamic acid tert-butyl ester:

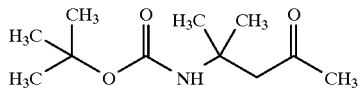

Diacetonamine hydrogen oxalate (30.0 g; 146 mmol) was suspended in tetrahydrofuran (400 ml). An aqueous solution of sodium hydroxide (1N; 146 ml) was added. Di-tert-butyl dicarbonate (38.3 g; 175 mmol) was dissolved in tetrahydrofuran (100 ml) and added dropwise to the reaction mixture. The reaction mixture was stirred for 2 hours at room temperature. Sodium hydroxide (1N; 146 ml) was added and the reaction mixture was stirred for 12 h at room temperature. Water (200 ml) and ethyl acetate (200 ml) were added. The aqueous phase was extracted with ethyl acetate (4×200 ml). The combined organic phases were dried over magnesium sulfate and the solvent was removed in vacuo. The residue was chromatographed on silica (6×40 cm) using ethyl acetate/heptane (1:3) as eluent to afford 28.4 g of (1,1-dimethyl-3-oxobutyl)carbamic acid tert-butyl ester.

$^1$H-NMR (CDCl$_3$) δ1.34 (s, 6H); 1.42 (s, 9H); 2.14 (s, 3H); 2.86 (s, 2H); 4.85 (s, 1H).

(E)-5-tert-Butoxycarbonylamino-3,5-dimethylhex-2-enoic acid ethyl ester:

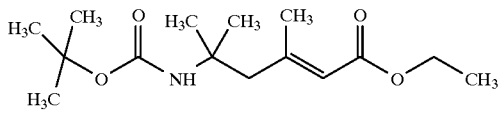

Triethyl phosphonoacetate (4.7 g; 20.9 mmol) was dissolved in tetrahydrofuran (36 ml). Potassium tert-butoxide (2.3 g; 20.9 mmol) was added and the reaction mixture was stirred for 40 min at room temperature. (1,1-Dimethyl-3-oxobutyl)carbamic acid tert-butyl ester (2.5 g; 11.6 mmol) was dissolved in tetrahydrofuran (15 ml) and added dropwise to the reaction mixture which was heated to reflux for 12 h. Ethyl acetate (100 ml) and hydrochloric acid (1N; 100 ml) were added and the phases were separated. The aqueous phase was extracted with ethyl acetate (3×50 ml). The combined organic phases were washed with an aqueous solution of sodium hydrogen carbonate (saturated; 100 ml), dried over magnesium sulfate and evaporated in vacuo. The residue was chromatographed on silica (3×40 cm) using ethyl acetate/heptane (1:2) as eluent to afford 2.0 g of (E)-5-tert-butoxycarbonylamino-3,5-dimethylhex-2-enoic acid ethyl ester.

$^1$H-NMR (CDCl$_3$): δ1.25 (t, 3H); 1.30 (s, 6H); 1.44 (s, 9H); 2.21 (s, 3H); 2,58 (s, 2H); 4.14 (q, 2H); 4.48 (s, 1H; 5.65 (s, 1H).

(2E)-5-tert-Butoxycarbonylamino-3,5-dimethylhex-2-enoic acid:

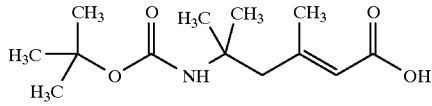

(E)-5-tert-Butoxycarbonylamino-3,5-dimethylhex-2-enoic acid ethyl ester (1.95 g; 6.83 mmol) was dissolved in 1,4-dioxane (25 ml) and water (15 ml). Lithium hydroxide (0.18 g; 7.52 mmol) was added and the reaction mixture was stirred for 12 h at room temperature. Water (150 ml) and tert-butyl methyl ether (150 ml) was added. The aqueous phase was diluted with an aqueous solution of sodium hydrogensulfate (10%) until pH 2.5 and extracted with tert-butyl methyl ether (3×100 ml). The combined organic phases were dried over magnesium sulfate and evaporated in vacuo. The residue was recrystallized from heptane (20 ml) to afford 0.6 g of (2E)-5-tert-butoxycarbonylamino-3,5-dimethylhex-2-enoic acid.

$^1$H-NMR (CDCl$_3$) δ1.29 (s, 6H); 1.44 (s, 9H); 2.23 (s, 3H); 2.62 (s, 2H); 4.45 (s, 1H); 5.66 (s, 1H).

The remaining synthesis proceeded similarly as in Example 1 to afford the title compound. (2E)-5-tert-Butoxycarbonylamino-3,5-dimethylhex-2-enoic acid was used in the last coupling step instead of (2E)-5-tert-butoxycarbonylamino-5-methylhex-2-enoic acid.

$^1$H-NMR (CDCl$_3$) (selected peaks for major rotamer) δ1.37 (s, 6H); 2.09 (s, 2H); 2.50 (s, 3H); 2.78 (s, 3H); 4.67 (dd, 1H); 5.05 (dd, 1H); 5.89 (s, 1H).

ESMS: m/z 541.7 (M+H)$^+$

HPLC (A1): r$_t$: 32.40 min

Example 3

(2E)-5-Methyl-5-(methylamino)hex-2-enoic acid N-((1R)-1-((2R)-2-benzyl-3-oxo-piperazine-1-carbonyl)-2-(2-naphthyl)ethyl)-N-methylamide.

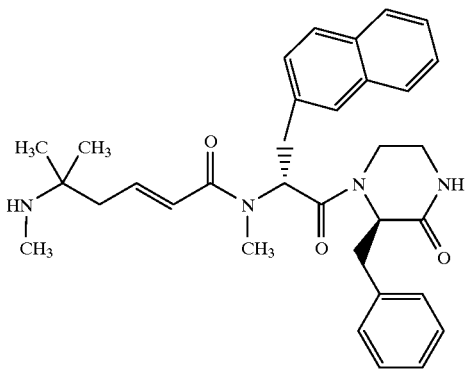

(2E)-5-(N-(tert Butoxycarbonyl)-N-methylamino)-5-methylhex-2-enoic acid.

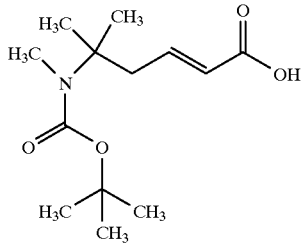

(2E)-5-(tert-Butyloxycarbonylamino)-5-methylhex-2-enoic acid (5.00 g; 20.6 mmol) was dissolved in tetrahydrofuran (70 ml). Methyl iodide (10.3 ml; 164 mmol) was added and the solution was cooled to 0° C. Sodium hydride (60% in oil) (2.07 g; 61.6 mmol) was added in portions and the solution was stirred at room temperature for four days. Ethyl acetate (70 ml) and water (60 ml) were added dropwise and the solvent was removed in vacuo. The crude product was dissolved in water (40 ml) and diethyl ether (40 ml). The organic phase was washed with a saturated aqueous solution of sodium hydrogencarbonate (30 ml). The aqueous phases were mixed and 5% aqueous citric acid was added to pH 3. The aqueous phase was extracted with ethyl acetate (4×50 ml). The combined organic extracts were washed with water (2×40 ml), an aqueous solution of sodium thiosulfate (5%; 40 ml), water (40 ml), dried over $MgSO_4$ and the solvent was removed in vacuo. The residue was dissolved in ethyl acetate (45 ml) and washed with an aqueous solution of sodium hydrogensulfate (10%; 3×30 ml), dried over magnesium sulfate and concentrated in vacuo to give 4.00 g of (2E)-5-(N-(tert-butoxycarbonyl)-N-methylamino)-5-methylhex-2-enoic acid.

$^1$H-NMR (CDCl$_3$) δ1.38 (s, 6H), 1.45 (s, 9H ); 2.80 (d, 2H); 2.85 (s, 3H); 5.88 (d, 1H); 7.01 (q, 1H ).

The remaining synthesis proceeded similarly as in Example 1 substituting (2E)-5-(tert-butyloxycarbonylamino)-5-methylhex-2-enoic acid with (2E)-5-(N-(tert-butoxycarbonyl)-N-methylamino)-5-methylhex-2-enoic acid in the last coupling step to afford the title compound.

$^1$H-NMR (CDCl$_3$) (selected peaks for major rotamer) δ1.38 (s, 3H); 1.44 (s, 3H); 2.69 (s, 3H); 2.88 (s, 3H); 4.44 (dd, 1 H); 4.52 (dd, 1 H); 6.34 (d, 1 H).

ESMS: m/z 541.9 (M+H)$^+$

HPLC (A1): r$_t$: 31.37 min

Example 4

(2E)-5-Methyl-5-methylaminohex-2-enoic acid N-((1R)-1-((2R,5R)-2-benzyl-5-methyl-3-oxopiperazine-1-carbonyl)-2-(2-naphthyl)ethyl)-N-methylamide.

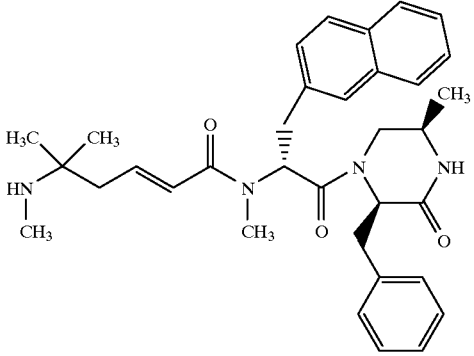

This compound was prepared using the procedure in Example 1 and 3. L-Boc-alaninal was used instead of Boc-glycinal.

$^1$H-NMR (CDCl$_3$): (selected peaks for major rotamer) δ1.21 (d, 3H); 1.32 (s, 3H); 1.40 (s, 3H); 2.63 (s, 3H); 2.88 (s, 3H); 4.42 (dd, 1H); 4.60 (dd, 1H); 6.26 (d, 1H).

ESMS: m/z 555.9 (M+H)$^+$

HPLC (A1): r$_t$: 32.30 min.

Example 5

(2E)-5-Amino-5-methylhex-2-enoic acid N-((1R)-2-((2R)-2-benzyl-4-methyl-3-oxopiperazin-1-yl)-1-((2-naphthyl)methyl)-2-oxoethyl)-N-methylamide

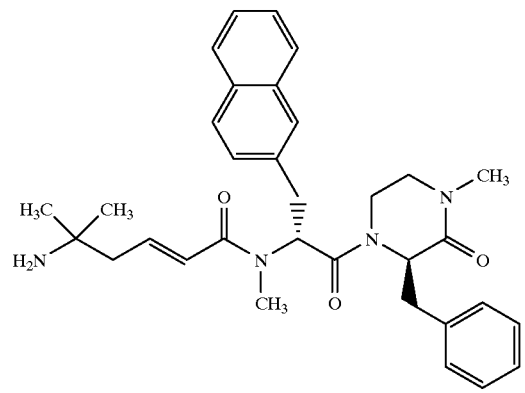

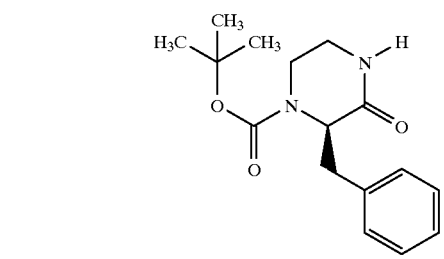

(3R)-4-tert-Butyloxycarbonyl-3-benzylpiperazin-2-one
(3R)-3-benzylpiperazin-2-one (from Example 1) (1.3 g) was dissolved in THF (20 ml) and aqueous sodium hydroxide (1M, 7 ml) was added. Boc-anhydride (1.8 g) was dissolved in THF (10 ml) and added dropwise. The mixture was stirred overnight. THF was removed in vacuo. Water (10 ml) was added and the aqueous phase was extracted with ethyl acetate (2×50 ml). The combined organic phases were dried (magnesium sulphate) and the solvent was removed in vacuo and the residue was chromatographed on Silica using ethyl acetate as eluent to afford 750 mg of 3R-4-tert-butyloxycarbonyl-3-benzylpiperazin-2-one.

$^{1}$H-NMR (CDCl$_{3}$) (major rotamer): δ1.31 (s, 9H); 2.85 (t, 1H); 3.10 (m, 2H; 3.25 (m, 2H); 3.42 (t, 2H); 4.80 (m, 1H); 6.40 (s, 1H); 7.12–7.35 (5 arom.H).

(3R)-4-tert-Butyloxycarbonyl-1-methyl-3-benzylpiperazin-2-one.

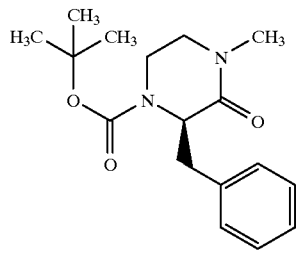

(3R)-4-tert-Butyloxycarbonyl-3-benzylpiperazin-2-one (see Example 1) (400 mg; 1.4 mmol) was added to a mixture of KOH (300 mg; 5.5 mmol) and DMSO (3 ml). Methyl iodide (400 mg 2.7 mmol) was added and the mixture was stirred for 1 h. Methylene chloride (20 ml) was added and the organic phase was washed with water (5×10 ml). The solvent was removed in vacuo to afford 220 mg of (3R)-4-tert-butyloxycarbonyl-1-methyl-3-benzylpiperazin-2-one.

$^{1}$H-NMR (CDCl$_{3}$) δ1.21 (s, 9H); 2.97 (s, 3H); 4.13 (dd,1H).

The remaining steps were performed similarly as in example 1 to afford the title compound.

$^{1}$H-NMR (CDCl$_{3}$) (selected peaks for major rotamer) δ1.15 (s, 6H); 2.30 (d, 2H); 2.54 (s, 3H); 2.74 (s, 3H); 4.05 (dd, 1H); 5.72 (dd, 1H); 6.19 (d, 1H).

ESMS: m/z 541.9 (M+H)$^{+}$

HPLC (A1): r$_{t}$: 27.70 min

Example 6

(2E)-5-Methyl-5-aminohex-2-enoic acid N-((1R)-1-((2R,5R)-2-benzyl-5-methyl-3-oxopiperazine-1-carbonyl)-2-(2-naphthyl)ethyl)-N-methylamide.

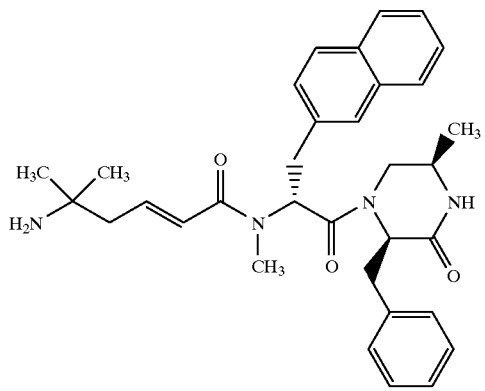

The title compound was prepared using the procedure in Example 1 and 4.

$^{1}$H-NMR (CDCl$_{3}$): δ1.09 (d, 3H); 1.31 (s, 6H); 2.74 (s, 3H); 5.12 (dd, 1H); 6.18 (d, 1H).

ESMS: m/z 541.7 (M+H)$^{+}$

HPLC (A1): r$_{t}$: 32.12 min.

Example 7

(2E)-4-(1-Aminocyclobutyl)but-2-enoic acid N-methyl-N-((1R)-2-(2-naphthyl)-1-((2R)-3-oxo-2-((2-thienyl)methyl)piperazine-1-carbonyl)ethyl)amide

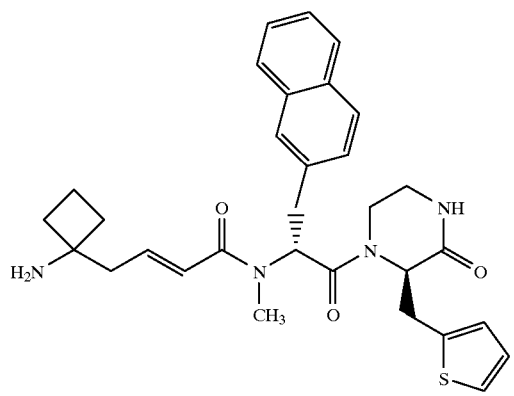

The title compound was prepared using the procedure in Schoen et al. J. Med. Chem., 1994, vol. 37, p. 897–906 substituting isobutylene with methylene cyclobutane and D-phenylalanine with D-thienylalanine.

$^{1}$H-NMR (CDCl$_{3}$): δ3.01 (s, 3H); 4.76 (dd, 1H); 5.15 (t, 1H); 6.34 (d, 1H)

ESMS: m/z 546.0 (M+H)$^{+}$

HPLC (A1): r$_{t}$: 31.05 min.

Example 8

(2E)-5-Amino-5-methylhex-2-enoic acid N-((1R)-2-((2R)-2-benzyl-3-oxo-piperazin-1-yl)-1-((biphenyl-4-yl)methyl)-2-oxoethyl)-N-methylamide.

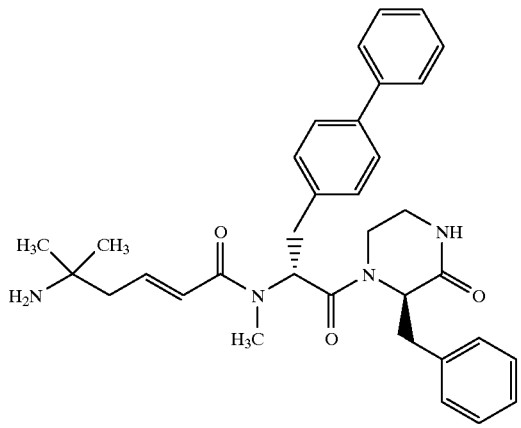

The title compound was prepared using the procedure in Example 1 using 4,4'-biphenylalanine instead of 2-napthylalanine.

¹H-NMR (CDCl₃): δ1.18 (s, 6H); 2.77 (s, 1H); 5.31 (dd, 1H); 5.72 (dd, 1H); 6.21 (dd, 1H).

ESMS: m/z 554.1 (M+H)⁺

HPLC (A1): $r_t$: 34.62

Example 9

(2E)-4-(1-Ampinocyclobutyl)but-2-enoic acid N-((1R)-2-((2R,5R)-2-benzyl-5-methyl-3-oxopiperazin-1-yl)-1-((2-naphthyl)methyl)-2-oxoethyl)-N-methylamide

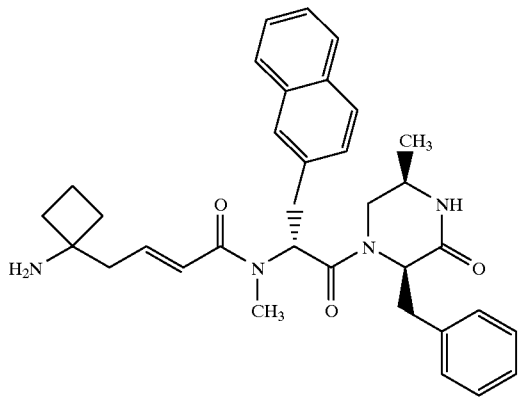

The title compound was prepared as in Schoen et al. J. Med. Chem., 1994, vol. 37, p. 897–906 substituting isobutylene with methylene cyclobutane and Boc-D-alaninal instead of Boc-glycinal.

¹H-NMR (CDCl₃): δ (selected peaks) 1.11 (d, 3H); 2.66 (s, 3H); 4.97 (dd, 1H); 5.85 (dd, 1H); 6.24 (d, 1H); 6.86 (m, 1H)

ESMS: m/z 554.0 (M+H)⁺

HPLC (A1): $r_t$: 32.3 min.

Example 10

(2E)-5-Methyl-5-methylamino-hex-2-enoic acid N-methyl-N-((1R)-1-(2-naphthyl)methyl-2-oxo-2-((2R)-3-oxo-2-((2-thienyl)methyl)piperazin-1-yl)ethyl)amide

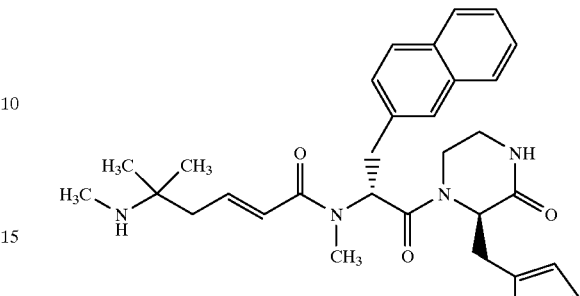

The title compound was prepared similarly as in Example 1 substituting D-phenylalanine with D-thienylalanine.

¹H-NMR (CDCl₃): δ1.38 (s, 3H); 1.41 (s, 3H); 2.65 (s, 3H); 2.91 (s, 3H); 4.47 (dd, 1H);

ESMS: m/z 547.0 (M+H)⁺

HPLC (A1): $r_t$: 31.15 min.

Example 11

(2E)-5-Amino-5-methylhex-2-enoic acid N-((1R)-2-((2R)-2-benzyl-4-methane-sulfonyl-piperazin-1-yl)-1-(naphth-2-ylmethyl)-2-oxoethyl)-N-methylamide.

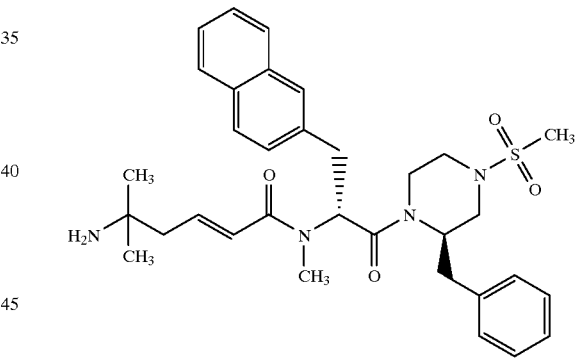

(3R)-3,4-Dibenzylpiperazin-2-one.

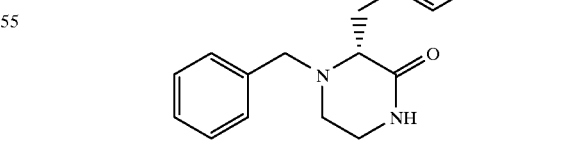

(3R)-3-Benzylpiperazin-2-one (4.1 g; 21.6 mmol, prepared as described in Example 1) was dissolved in methanol (40 ml). Benzaldehyde (2.3 g; 21.6 mmol) was added followed by 4 Å molsieves (2 g) and the mixture was stirred under an atmosphere of nitrogen for ½ h. Acetic acid (1.2 ml) was added and sodium cyanoborohydride (2.0 g; 32.4 mmol) was added portion wise during 20 minutes. The reaction mixture was stirred overnight and the filtered. From the filtrate the solvent was evaporated and the residue was dissolved into ethyl acetate (15 ml) and purified on silica gel using ethyl acetate as eluent. This afforded 2.6 g of (3R)-3,4-dibenzylpiperazin-2-one.

¹H-NMR (CDCl₃): δ2.50 (m, 1H); 2.95 (m, 1H); 3.08 (m, 1H); 3.15–3.45 (m, 4H); 3.48 (d, 1H); 3.96 (d, 1H); 6.18 (s, 1H); 7.1–7.3 (m, 10H).

(2R)-1,2-Dibenzylpiperazine.

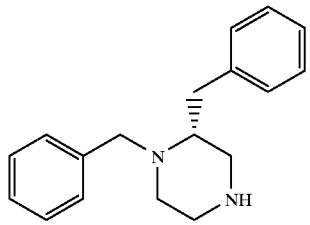

A solution of (3R)-3,4-dibenzylpiperazin-2-one (2.5 g; 9.0 mmol) in dry tetrahydrofuran (30 ml) was placed under an atmosphere of nitrogen and stirred on an ice-bath. Lithium aluminiumhydride (5.0 ml; 1.0M in tetrahydrofuran) was added dropwise during 15 minutes. The mixture was then heated at reflux temperature for 2 h and then allowed top cool. Another portion of lithium aluminiumhydride (4.0 ml; 1.0M in tetrahydrofuran) was added and the mixture was refluxed for 1 h. The mixture was allowed to cool and then quenched with water and a 4N sodium hydroxide solution. Ethyl acetate (50 ml) was added and the mixture was filtered. The solvent was evaporated in vacuo to give 2.0 g of (2R)-1,2-dibenzylpiperazine.

¹H-NMR (CDCl₃): δ2.20 (m, 1H); 2.55–2.82 (m, 7H); 3.15 (dd, 1H); 3.42 (d, 1H); 4.10 (d, 1H); 7.1–7.4 (m, 10H).

(2R)-1,2-Dibenzyl-4-methanesulfonylpiperazine.

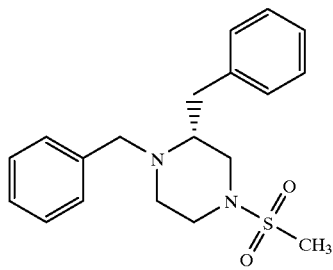

To a stirred solution of (2R)-1,2-dibenzylpiperazine (2.0 g; 7.5 mmol) in dichloromethane (30 ml), methanesulfonyl chloride (0.86 g; 7.5 mmol) was added and the mixture was stirred at ambient temperature for 1 h. Potassium carbonate (1.1 g) was added and stirring was continued for another hour. Dichloromethane (20 ml) and water (10 ml) were added and the phases were separated. The organic phase was washed with water (10 ml) and dried over magnesium sulfate. The solvent was evaporated in vacuo to give 2.2 g of (2R)-1,2-dibenzyl-4-methanesulfonylpiperazine.

¹H-NMR (CDCl₃): δ2.58 (m, 1H); 2.72 (s, 3H); 2.85–3.10 (m, 6H); 3.27 (m, 1H); 3.45 (m, 1H); 3.72 (d, 1H); 3.95 (m, 1H); 7.1–7.4 (m, 10H).

(3R)-3-Benzyl-1-methanesulfonylpiperazine hydrochloride.

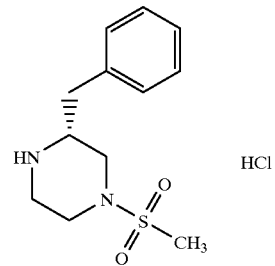

(2R)-1,2-Dibenzyl-4-methanesulfonylpiperazine (2.2 g; 6.4 mmol) was dissolved in dry 1,2-dichloroethane (20 ml) under an atmosphere of nitrogen. The mixture was placed on an ice-bath and a solution of α-chloroethyl chloroformate (1.0 g; 7.04 mmol) in dry 1,2-dichloroethane (10 ml) was added keeping the temperature between 0 and 5° C. When addition is complete stirring is continued for 15 minutes on the ice-bath. The reaction mixture is heated slowly to 90° C. on an oil-bath and heated at reflux temperature for 1 h. The major part of the solvent was allowed to evaporate and the residue was allowed to cool on an ice-bath. Methanol (20 ml) was added and the mixture was heated at reflux temperature for 1 h. The mixture was allowed to cool to ambient temperature, diethyl ether (30 ml) was slowly added and the mixture was stirred for 30 minutes. The solid was isolated by filtration, washed with diethyl ether, and dried to give 0.78 g of (3R)-3-benzyl-1-methanesulfonylpiperazine hydrochloride. M.p. 204–208° C.

¹H-NMR (DMSO-d₆): δ2.87–3.25 (m, 8H); 3.35–3.65 (m, 4H); 7.25–7.40 (m, 5H).

N-[(1R)-2-((2R)-2-Benzyl-4-methanesulfonylpiperazin-1-yl)-1-(naphth-2-ylmethyl)-2-oxoethyl]-N-methylcarbamic acid tert-butyl ester.

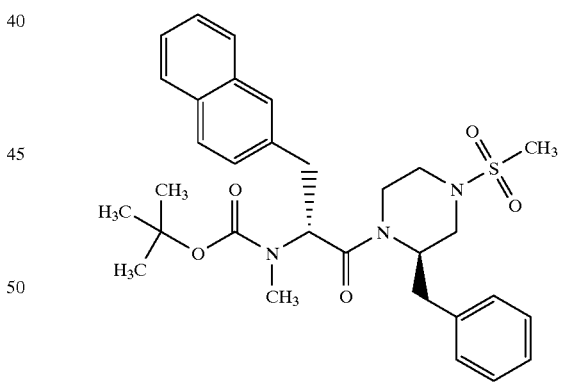

(2R)-(tert-Butoxycarbonylmethylamino)-3-(2-naphthyl)propionic acid (0.86 g; 2.6 mmol) was dissolved into dichloromethane (25 ml) and placed under an atmosphere of nitrogen. (3R)-3-Benzyl-1-methanesulfonylpiperazine hydrochloride (0.75 g; 2.6 mmol), N-methylmorpholine (0.26 g; 2.6 mmol), 1-hydroxy-7-azabenzotriazole (0.39 g; 2.9 mmol) and N-(3-dimethylaminopropyl)-N'-ethylcarbodiimide hydrochloride (0.55; 2.9 mmol) were added and the mixture was stirred overnight at ambient temperature. Dichloromethane (25 ml) was added and the mixture was washed with water (3×15 ml) and dried over magnesium sulfate. The solvent was evaporated in vacuo to give 1.3 g of an oily residue which was chromatographed on silica gel using a mixture of heptane and ethyl acetate (1:1) as eluent. This afforded 0.65 g of N-[(1R)-2-((2R)-2-benzyl-4-methanesulfonylpiperazin-1-yl)-1-(naphth-2-ylmethyl)-2-oxo-ethyl]-N-methylcarbamic acid tert-butyl ester as a solid.

M.p. 76–80° C.

(2R)-1-((2R)-2-Benzyl-4-methanesulfonyl-piperazin-1-yl)-2-methylamino-3-(naphth-2-yl)-propan-1-one.

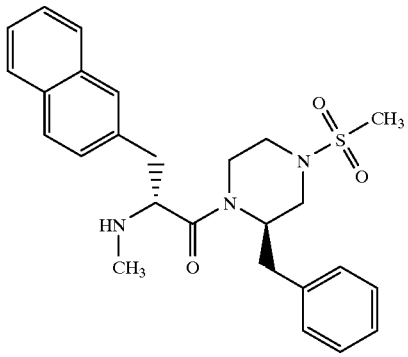

N-[(1R)-2-((2R)-2-Benzyl4-methanesulfonylpiperazin-1-yl)-(1R)-1-(naphth-2-ylmethyl)-2-oxo-ethyl]-N-methylcarbamic acid tert-butyl ester (0.63 g; 1.1 mmol) was dissolved into dichloromethane (10 ml) with stirring and placed under an atmosphere of nitrogen. Trifluoroacetic acid (10 ml) was added and the mixture was stirred for 15 minutes. The reaction mixture was diluted with dichloromethane (75 ml) and placed on an ice-bath. Saturated aqueous sodium bicarbonate solution was added and then an aqueous potassium carbonate solution until pH 10. The phases were separated and the aqueous phase was extracted with dichloromethane (50 ml). The combined organic extracts were dried over magnesium sulfate and the solvent was evaporated in vacuo. This afforded 0.51 g of (2R)-1-((2R)-2-benzyl-4-methanesulfonyl-piperazin-1-yl)-2-methylamino-3-(naphth-2-yl)propan-1-one as a solid.

M.p. 165–168° C.

((3E)-4-(N-((1R)-2-((2R)-2-Benzyl-4-methanesulfonyl-piperazin-1-yl)-1-(naphth-2-yl-methyl)-2-oxo-ethyl)-N-methylcarbamoyl)-1,1-dimethyl-but-3-enyl)carbamic acid tert-butyl ester.

(2E)-5-(tert-Butyloxycarbonylamino)-5-methylhex-2-enoic acid (0.49 g; 2.0 mmol) was dissolved into dichloromethane (10 ml) and placed under an atmosphere of nitrogen. 1-Hydroxy-7-azabenzotriazole (2.0 mmol) and N-(3-dimethylaminopropyl)-N'-ethylcarbodiimide hydrochloride (2.0 mmol) were added and the mixture was stirred for 15 minutes. A solution of 1-((2R)-2-benzyl-4-methanesulfonyl-piperazin-1-yl)-(2R)-2-methylamino-3-naphth-2-yl-propan-1-one (0.51 g; 1.1 mmol) in dichloromethane (10 ml) was added and the mixture was stirred overnight. Dichloromethane (50 ml) was added and the mixture was washed with water (2×50 ml). The combined aqueous phases were extracted with dichloromethane (50 ml). The combined organic extracts were dried over magnesium sulfate and the solvent was evaporated in vacuo. This afforded 1.0 g residue which was chromatographed on silica gel using a mixture of heptane and ethyl acetate (3:7) as eluent. This afforded 0.55 g of ((3E)-4-(N-((1R)-2-((2R)-2-benzyl-4-methanesulfonyl-piperazin-1-yl)-1-(naphth-2-yl-methyl)-2-oxoethyl)-N-methylcarbamoyl)-1,1-dimethylbut-3-enyl)carbamic acid tert-butyl ester.

TLC; Rf=0.33 (heptane/ethyl acetate=3:7).

((3E)-4-(N-((1R)-2-((2R)-2-Benzyl-4-methanesulfonyl-piperazin-1-yl)-1-(naphth-2-ylmethyl)-2-oxoethyl)-N-methyl-carbamoyl)-1,1-dimethylbut-3-enyl)carbamic acid tert-butyl ester (0.54 g; 0.78 mmol) was dissolved in dry dichloromethane (10 ml) with stirring and trifluoroacetic acid (10 ml) was added. The mixture was stirred for 8 min. at ambient temperature and then diluted with dichloromethane (50 ml). The mixture was placed on an ice-bath and saturated aqueous sodium bicarbonate solution was added and then an aqueous potassium carbonate solution until pH 10. The phases were separated and the aqueous phase was extracted with dichloromethane (20 ml). The combined organic extracts were dried over magnesium sulfate and the solvent was evaporated in vacuo. This afforded 0.33 g of (2E)-5-amino-5-methylhex-2-enoic acid N-((1R)-2-((2R)-2-benzyl-4-methanesulfonyl-piperazin-1-yl)-1-(naphth-2-ylmethyl)-2-oxoethyl)-N-methylamide.

$^1$H-NMR (CDCl$_3$): δ1.17 (s, 3H); 1.20 (s, 3H); 1.8–3.65 (complex m); 4.10 (d, 1H); 4.55+4.88 (d+m, 1H); 5.82+6.03 (t+dd, 1H); 6.28 (dd, 1H); 6.81+6.95 (dt+dt, 1H); 7.15–7.80 (m, 12H).

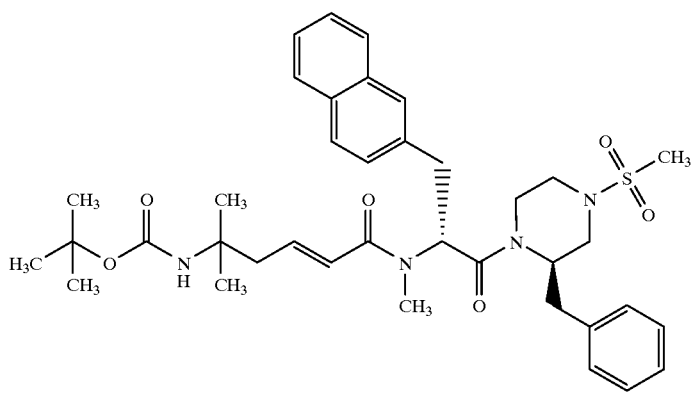

We claim:

1. A compound of formula I

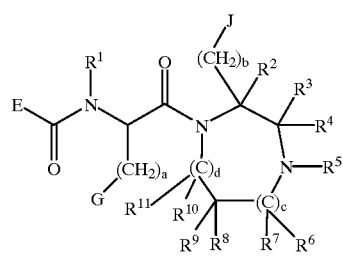

formula I wherein

R$^1$ is hydrogen, or C$_{1-6}$-alkyl optionally substituted with aryl;

a and b are independently 1 or 2;

c+d is 1;

R$^2$, R$^3$, R$^4$, R$^6$, R$^7$, R$^8$, R$^9$, R$^{10}$, and R$^{11}$ are independently hydrogen, aryl optionally substituted with halogen, amino, C$_{3-6}$-cycloalkyl, hydroxy, aryl, —COOR$^{22}$, or —CONR$^{23}$R$^{24}$, or C$_{1-6}$-alkyl optionally substituted with halogen, amino, C$_{3-6}$-cycloalkyl, hydroxy, aryl, —COOR$^{22}$, or —CONR$^{23}$R$^{24}$;

R$^3$ and R$^4$ can be taken together to form =O or =S;

R$^8$ and R$^9$ can be taken together to form =O or =S;

R$^5$ is hydrogen,

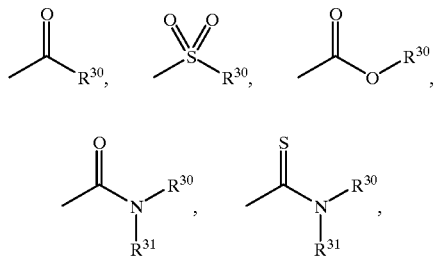

or C$_{1-6}$-alkyl optionally substituted with aryl, hydroxy, C$_{3-6}$-cycloalkyl, amino, —COOR$^{25}$, —CONR$^{26}$R$^{27}$, —NR'R",

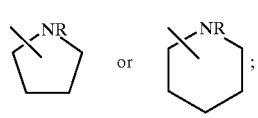

R, R' and R" are independently hydrogen or C$_{1-6}$-alkyl;

R$^{30}$ and R$^{31}$ are C$_{1-6}$-alkyl optionally substituted with aryl, hydroxy, C$_{3-6}$-cycloalkyl, or amino;

R$^{22}$, R$^{23}$, R$^{24}$, R$^{25}$, R$^{26}$, and R$^{27}$ are independently hydrogen or C$_{1-6}$-alkyl;

when R$^3$ and R$^4$ are taken together to form =O or =S, E is

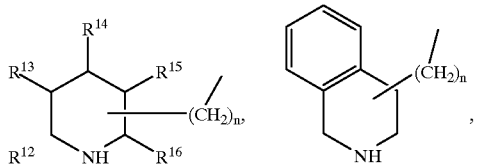

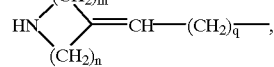

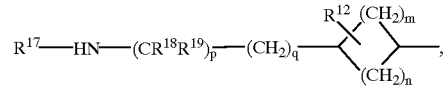

or

R$^{17}$NH—(CR$^{18}$R$^{19}$)$_p$—(CH$_2$)$_m$—M—(CHR$^{20}$)$_o$—(CH$_2$)$_n$—;

when R$^3$ or R$^4$ is hydrogen, aryl optionally substituted with halogen, amino, C$_{3-6}$-cycloalkyl, hydroxy, aryl, —COOR$^{22}$, or —CONR$^{23}$R$^{24}$, or C$_{1-6}$-alkyl optionally substituted with halogen, amino, C$_{3-6}$-cycloalkyl, hydroxy, aryl, —COOR$^{22}$, or —CONR$^{23}$R$^{24}$, E is

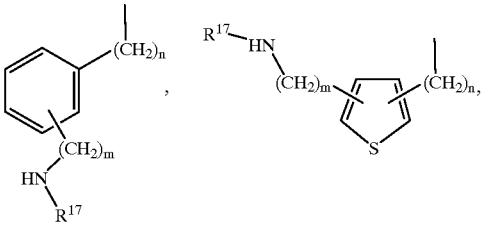

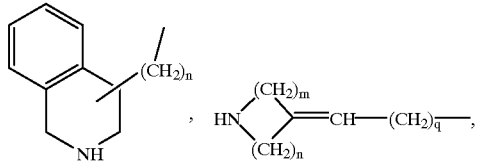

or

R$^{17}$NH—(CR$^{18}$R$^{19}$)$_p$—(CH$_2$)$_m$—Q—(CHR$^{20}$)$_o$—(CH$_2$)$_n$—;

R$^{12}$, R$^{13}$, R$^{14}$, R$^{15}$, R$^{16}$, R$^{17}$ and R$^{20}$ are independent hydrogen or C$_{1-6}$-alkyl optionally substituted with halogen, amino, hydroxyl or aryl;

$R^{18}$ and $R^{19}$ are independently hydrogen or $C_{1-6}$-alkyl optionally substituted with halogen, amino or hydroxyl;

any two of $R^{17}$, $R^{18}$, and $R^{19}$ can independently be joined together to form an $C_{1-6}$-alkylene bridge;

n, m and q are independently 0, 1, 2, or 3;

o and p are independently 0 or 1;

M is —CH=$CR^{21}$—, —O—, —S—, or a valence bond;

Q is —CH=$CR^{21}$—, —O—, or —S—;

$R^{21}$ is hydrogen or $C_{1-6}$-alkyl optionally substituted with halogen, amino, hydroxyl or aryl;

G is hydrogen,

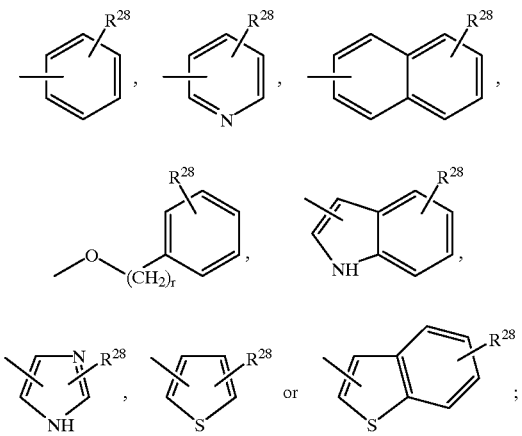

wherein $R^{28}$ is hydrogen, halogen, $C_{1-6}$-alkyl, $C_{1-6}$-alkoxy or aryl;

r is 0, 1, or 2;

J is hydrogen,

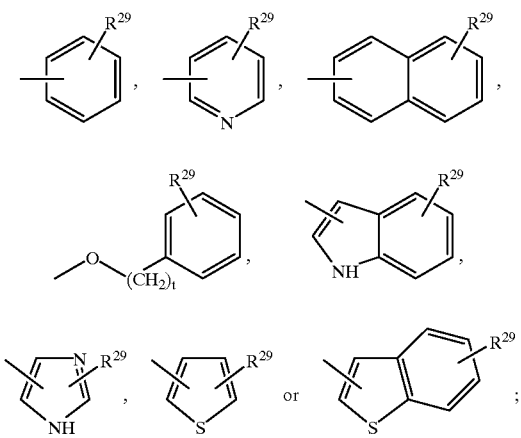

wherein $R^{29}$ is hydrogen, halogen, $C_{1-6}$-alkyl, $C_{1-6}$-alkoxy or aryl;

t is 0, 1, or 2;

or a pharmaceutically acceptable salt thereof.

2. A compound of formula II

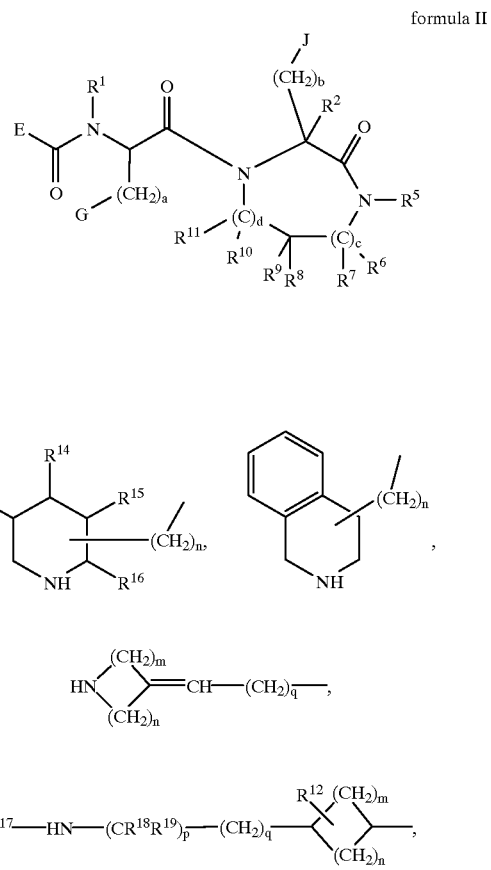

formula II wherein

E is

[structures]

or $R^{17}NH$—$(CR^{18}R^{19})_p$—$(CH_2)_m$—M—$(CHR^{20})_o$—$(CH_2)_n$—;

$R^{12}$, $R^{13}$, $R^{14}$, $R^{15}$, $R^{16}$, $R^{17}$ and $R^{20}$ are independently hydrogen or $C_{1-6}$-alkyl optionally substituted with halogen, amino, hydroxyl or aryl;

$R^{18}$ and $R^{19}$ are independently hydrogen or $C_{1-6}$-alkyl optionally substituted with halogen, amino or hydroxyl;

any two of $R^{17}$, $R^{18}$, and $R^{19}$ can independently be joined together to form an $C_{1-6}$-alkylene bridge;

n, m and q are independently 0, 1, 2, or 3;

o and p are independently 0 or 1;

M is —CH=$CR^{21}$—, —O—, —S—, or a valence bond;

$R^{21}$ is hydrogen or $C_{1-6}$-alkyl optionally substituted with halogen, amino, hydroxyl or aryl; and $R^1$, $R^2$, $R^5$, $R^6$, $R^7$, $R^8$, $R^9$, $R^{10}$, $R^{11}$, G, J, a, b, c, and d are defined as in claim 1;

or a pharmaceutically acceptable salt thereof.

43

3. The compound of formula III formula III

[Structure of formula III showing R$^1$, E, G, (CH$_2$)$_a$, R$^9$, R$^8$, R$^7$, R$^6$, R$^5$, J, (CH$_2$)$_b$, R$^2$]

wherein E is

[Structures showing various E groups with R$^{12}$, R$^{13}$, R$^{14}$, R$^{15}$, R$^{16}$, NH, (CH$_2$)$_n$]

[Structure with HN, (CH$_2$)$_m$, (CH$_2$)$_n$, CH—(CH$_2$)$_q$—]

[Structure: R$^{17}$—HN—(CR$^{18}$R$^{19}$)$_p$—(CH$_2$)$_q$—, with R$^{12}$, (CH$_2$)$_m$, (CH$_2$)$_n$]

[Phenyl structure with (CH$_2$)$_n$, (CH$_2$)$_m$, HN, R$^{17}$]

[Thiophene structure with R$^{17}$-HN, (CH$_2$)$_m$, (CH$_2$)$_n$]

or

R$^{17}$NH—(CR$^{18}$R$^{19}$)$_p$—(CH$_2$)$_m$—M—(CHR$^{20}$)$_o$—(CH$_2$)$_n$—;

R$^{12}$, R$^{13}$, R$^{14}$, R$^{15}$, R$^{16}$, R$^{17}$ and R$^{20}$ are independently hydrogen or C$_{1-6}$-alkyl optionally substituted with halogen, amino, hydroxyl or aryl;

R$^{18}$ and R$^{19}$ are independently hydrogen or C$_{1-6}$-alkyl optionally substituted with halogen, amino or hydroxyl;

any two of R$^{17}$, R$^{18}$, and R$^{19}$ can independently be joined together to form an C$_{1-6}$-alkylene bridge;

n, m and q are independently 0, 1, 2, or 3;

o and p are independently 0 or 1;

M is —CH=CR$^{21}$—, —O—, —S—, or a valence bond;

R$^{21}$ is hydrogen or C$_{1-6}$-alkyl optionally substituted with halogen, amino, hydroxyl or aryl;

R$^8$ and R$^9$ are independently hydrogen, aryl optionally substituted with halogen, amino, C$_{3-6}$-cycloalkyl, hydroxy, aryl, —COOR$^{22}$, or —CONR$^{23}$R$^{24}$, or C$_{1-6}$-alkyl optionally substituted with halogen, amino, C$_{3-6}$-cycloalkyl, hydroxy, aryl, —COOR$^{22}$, or —CONR$^{23}$R$^{24}$; and

44

G, J, R$^1$, R$^2$, R$^5$, R$^6$, R$^7$, R$^{22}$, R$^{23}$, R$^{24}$, a, and b are as defined in claim 1;

or a pharmaceutically acceptable salt thereof.

4. The compound according to claim 2 wherein R$^5$ is hydrogen or C$_{1-6}$-alkyl optionally substituted with aryl, hydroxy, C$_{3-6}$cycloalkyl, amino, —COOR$^{25}$, —CONR$^{26}$R$^{27}$, —NR'R"

[Structures of NR-pyrrolidine or NR-piperidine]

R, R' and R" are independently hydrogen or C$_{1-6}$-alkyl;

R$^{25}$, R$^{26}$, and R$^{27}$ are independently hydrogen or C$_{1-6}$-alkyl; and R$^1$, R$^2$, R$^3$, R$^4$, R$^6$, R$^7$, R$^8$, R$^9$, R$^{10}$, R$^{11}$, E, G, J, a, b, c, and d are as defined in any of the preceeding claims;

or a pharmaceutically acceptable salt thereof.

5. The compound according to claims 2, wherein
E is

[Structures showing E groups with R$^{12}$, R$^{13}$, R$^{14}$, R$^{15}$, R$^{16}$, NH, (CH$_2$)$_n$]

[Structure with HN, (CH$_2$)$_m$, (CH$_2$)$_n$, CH—(CH$_2$)$_q$—]

[Structure: R$^{17}$—HN—(CR$^{18}$R$^{19}$)$_p$—(CH$_2$)$_q$—, with R$^{12}$, (CH$_2$)$_m$, (CH$_2$)$_n$]

[Phenyl structure with (CH$_2$)$_n$, (CH$_2$)$_m$, HN, R$^{17}$]

[Thiophene structure with R$^{17}$-HN, (CH$_2$)$_m$, (CH$_2$)$_n$]

or

R$^{17}$NH—(CR$^{18}$R$^{19}$)$_p$—(CH$_2$)$_m$—M—(CHR$^{20}$)$_o$—(CH$_2$)$_n$—;

R$^{12}$, R$^{13}$, R$^{14}$, R$^{15}$, R$^{16}$, R$^{17}$, R$^{18}$, R$^{19}$, and R$^{20}$ are independently hydrogen or methyl;

n, m and q are independently 0, 1, 2, or 3;

o and p are independently 0 or 1;

M is —CH=CR$^{21}$—, —O—, or a valence bond;

R$^{21}$ is hydrogen, methyl or benzyl; and

R$^1$, R$^2$, R$^3$, R$^4$, R$^5$, R$^6$, R$^7$, R$^8$, R$^9$, R$^{10}$, R$^{11}$, G, J, a, b, c, and d are as defined in any of the preceeding claims;

or a pharmaceutically acceptable salt thereof.

6. The compound according to claim 1 wherein
R$^3$ and R$^4$ are independently hydrogen, aryl optionally substituted with halogen, amino, C$_{3-6}$-cycloalkyl, hydroxy, aryl, —COOR²², or —CONR²³R²⁴, or $C_{1-6}$-alkyl optionally substituted with halogen, amino, $C_{3-6}$-cycloalkyl, hydroxy, aryl, —COOR²², or —CONR²³R²⁴;

$R^{22}$, $R^{23}$, and $R^{24}$ are independently hydrogen or $C_{1-6}$-alkyl;

E is

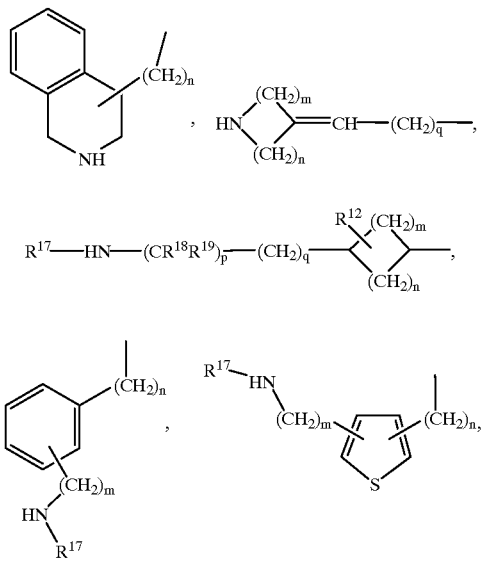

or $R^{17}NH$—$(CR^{18}R^{19})_p$—$(CH_2)_m$—Q—$(CHR^{20})_o$—$(CH_2)_n$—;

$R^{12}$, $R^{17}$ and $R^{20}$ are independently hydrogen or $C_{1-6}$-alkyl optionally substituted with halogen, amino, hydroxyl or aryl;

$R^{18}$ and $R^{19}$ are independently hydrogen or $C_{1-6}$-alkyl optionally substituted with halogen, amino or hydroxyl;

any two of $R^{17}$, $R^{18}$, and $R^{19}$ can independently be joined together to form an $C_{1-6}$-alkylene bridge;

n, m and q are independently 0, 1, 2, or 3;

o and p are independently 0 or 1;

Q is —CH=CR²¹—, —O—, or —S—;

$R^{21}$ is hydrogen or $C_{1-6}$-alkyl optionally substituted with halogen, amino, hydroxyl or aryl; and $R^1$, $R^2$, $R^5$, $R^6$, $R^7$, $R^8$, $R^9$, $R^{10}$, $R^{11}$, G, J, a, b, c, and d are as defined in claim 1 or a pharmaceutically acceptable salt thereof.

7. A compound of formula IV

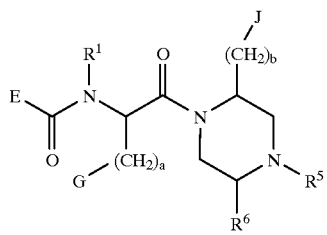
formula IV wherein E is

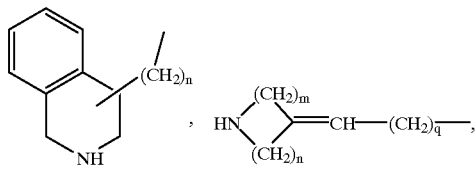

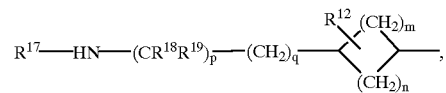

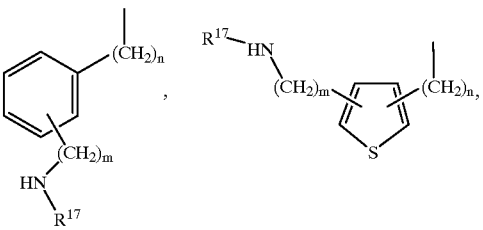

or

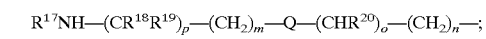

$R^{12}$, $R^{17}$ and $R^{20}$ are independently hydrogen or $C_{1-6}$-alkyl optionally substituted with halogen, amino, hydroxyl or aryl;

$R^{18}$ and $R^{19}$ are independently hydrogen or $C_{1-6}$-alkyl optionally substituted with halogen, amino or hydroxyl;

any two of $R^{17}$, $R^{18}$, and $R^{19}$ can independently be joined together to form an $C_{1-6}$-alkylene bridge;

n, m and q are independently 0, 1, 2, or 3;

o and p are independently 0 or 1;

Q is —CH=CR²¹—, —O—, or —S—;

$R^{21}$ is hydrogen or $C_{1-6}$-alkyl optionally substituted with halogen, amino, hydroxyl or aryl; and $R^1$, $R^5$, $R^6$, G, J, a, and b are as defined in claim 1;

or a pharmaceutically acceptable salt thereof.

8. A compound of formula V

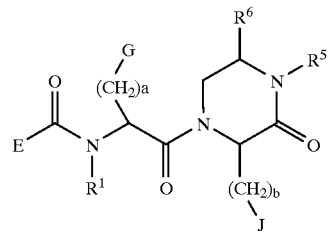
formula V wherein E is

[chemical structures showing various E group options with R¹², R¹³, R¹⁴, R¹⁵, R¹⁶, R¹⁷ substituents on piperidine, tetrahydroisoquinoline, and related ring systems]

or $R^{17}NH-(CR^{18}R^{19})_p-(CH_2)_m-M-CHR^{20}_o-(CH_2)_n-$;

$R^{12}$, $R^{13}$, $R^{14}$, $R^{15}$, $R^{16}$, $R^{17}$ and $R^{20}$ are independently hydrogen or $C_{1-6}$-alkyl optionally substituted with halogen, amino, hydroxyl or aryl;

$R^{18}$ and $R^{19}$ are independently hydrogen or $C_{1-6}$-alkyl optionally substituted with halogen, amino or hydroxyl;

any two of $R^{17}$, $R^{18}$, and $R^{19}$ can independently be joined together to form an $C_{1-6}$-alkylene bridge;

n, m and q are independently 0, 1, 2, or 3;

o and p are independently 0 or 1;

M is —CH=CR²—, —O—, —S—, or a valence bond;

$R^{21}$ is hydrogen or $C_{1-6}$-alkyl optionally substituted with halogen, amino, hydroxyl or aryl;

$R^5$ is hydrogen or $C_{1-6}$-alkyl optionally substituted with aryl, hydroxy, $C_{3-6}$-cycloalkyl, amino, —COOR²⁵, —CONR²⁶R²⁷, —NR'R",

[two chemical structures: pyrrolidine and piperidine with NR substituents]

R, R' and R" are independently hydrogen or $C_{1-6}$-alkyl;

$R^{25}$, $R^{26}$, and $R^{27}$ are independently hydrogen or $C_{1-6}$-alkyl; and G, J, a, b, $R^1$, and $R^6$ are as defined in claim 1;

or a pharmaceutically acceptable salt thereof.

9. The compound according to claim 1 wherein $R^1$ is hydrogen or methyl;

or a pharmaceutically acceptable salt thereof.

10. The compound according to claim 1 selected from the group consisting of (2E)-5-amino-5-methylhex-2-enoic acid N-((1R)-1-((2R)-2-benzyl-3-oxopiperazine-1-carbonyl)-2-(2-naphthyl)ethyl)-N-methylamide, (2E)-5-amino-5-methylhex-2-enoic acid N-((1R)-1-((2R)-2-benzyl-4-(cyclopropyl-methyl)-3-oxopiperazine-1-carbonyl)-2-(2-naphthyl)ethyl)-N-methylamide, (2E)-5-amino-5-methylhex-2-enoic acid N-((1R)-1-((2R,5R)-2-benzyl-5-(hydroxy-methyl-3-oxopiperazine-rcarbonyl)-2-(2-naphthyl)ethyl)-N-methylamide, (2E)-5-amino-5-methylhex-2-enoic acid N-((1R)-1-((2R)-2-benzyl-3-oxo-1,4-diazepane-1-carbonyl)-2-(2-naphthyl)ethyl)-N-methylamide, piperidine4-carboxylic acid N-methyl-N-((1R)-2-(2-naphthyl)-1-((2R)-2-((2-napthyl)methyl)-3-oxopiperazine-1-carbonyl)ethyl)amide, (2E)-5-amino-5-methylhex-2-enoic acid N-((1R)-1-((2R)-2-benzyl-4-(dimethylcarbamoylmethyl)-3-oxopiperazine-1-carbonyl)-2-(2-naphthyl)ethyl)-N-methylamide, (2E)-5-methyl-5-(methylamino)hex-2-enoic acid N-((1R)-1-((2R)-2-benzyl-3-oxo-piperazine-1-carbonyl)-2-(2-naphthyl)ethyl)-N-methylamide, (2E)-5-amino-5-methylhex-2-enoic acid N-((1R)-1-((2R,6S)-2-benzyl-6-methyl-3-oxopiperazine-1-carbonyl)-2-(2-naphthyl)ethyl)-N-methylamide, (2E)-5-amino-5-methylhex-2-enoic acid N-((1R)-1-((2R)-2-benzyl-3-oxopiperazine-1-carbonyl)-2-(biphenyl-4-yl)ethyl)-N-methylamide, (2E)-5-Amino-5-methylhex-2-enoic acid N-((1R)-1-((2R)-2-benzyl-3-oxopiperazine-1-carbonyl)-2-(2-naphthyl)ethyl)-N-methylamide, (2E)-5-amino-5-methylhex-2-enoic acid N-((1R)-1-((2R)-2-benzyl-4-methanesulfonylpiperazine-1-carbonyl)-2-benzyloxyethyl)-N-methylamide, (2E)-5-Amino-3,5-dimethylhex-2-enoic acid N-((1R)-1-((2R)-2-benzyl-3-oxo-piperazine-1-carbonyl)-2-(2-naphthyl)ethyl)-N-methylamide, (2E)-5-Methyl-5-methylaminohex-2-enoic acid N-((1R)-1-((2R,5R)-2-benzyl-5-methyl-3-oxopiperazine-1-carbonyl)-2-(2-naphthyl)ethyl)-N-methylamide, (2E)-5-Amino-5-methylhex-2-enoic acid N-((1R)-2-((2R)-2-benzyl-4-methyl-3-oxopiperazine-1-yl)-1-((2-naphthyl)methyl)-2-oxoethyl)-N-methylamide, (2E)-5-Methyl-5-aminohex-2-enoic acid N-((1R)-1-((2R,5R)-2-benzyl-5-methyl-3-oxopiperazine-1-carbonyl)-2-(2-naphthyl)ethyl)-N-methylamide, (2E)-4-(1-Aminocyclobutyl)but-2-enoic acid N-methyl-N-((1R)-2-(2-naphthyl)-1-((2R)-3-oxo-2-((2-thienyl)methyl)piperazine-1-carbonyl)ethyl)amide, (2E)-4-(1-Aminocyclobutyl)but-2-enoic acid N-((1R)-2-((2R,5R)-2-benzyl-5-methyl-3-oxopiperazin-1-yl)-1-((2-naphthyl)methyl)-2-oxoethyl)-N-methylamide, (2E)-5-Methyl-5-methylamino-hex-2-enoic acid N-methyl-N-((1R)-1-(2-naphthyl)methyl-2-oxo-2-((2R)-3-oxo-2-((2-thienyl)methyl)piperazin-1-yl)ethyl)amide, (2E)-5-Amino-5-methyl-hex-2-enoic acid N-((1R)-2-((2R)-2-benzyl-4-methanesulfonyl-piperazin-1-yl)-1-(naphth-2-ylmethyl)-2-oxo-ethyl)-N-methylamide, or a pharmaceutically acceptable salt thereof.

11. A pharmaceutical composition comprising, as an active ingredient, a compound according to claim 1 or a pharmaceutically acceptable salt thereof together with a pharmaceutically acceptable carrier or diluent.

12. The composition according to claim 11 in unit dosage form, comprising from about 10 to about 200 mg of the compound according to claim 11 or a pharmaceutically acceptable salt thereof.

* * * * *

UNITED STATES PATENT AND TRADEMARK OFFICE
CERTIFICATE OF CORRECTION

PATENT NO. : 5,919,777
DATED : July 6, 1999
INVENTOR(S) : Hansen et al

It is certified that error appears in the above-identified patent and that said Letters Patent is hereby corrected as shown below:

| | |
|---|---|
| Col. 39, line 23, claim 1 | claim 1, after " a and b are independently 1 or 2;" insert -- -- c and d are independently 0 or 1; --. |
| Col. 48, line 11, claim 10 | claim 10, change "rcarbonyl" and insert --1-carbonyl)--. |
| Col 48, line 30, claim 10 | claim 10, change "2-benzyl-3-oxopiperazine" and insert -- 2-benzyl-4 methanesulfonylpiperazine --. |

Signed and Sealed this

First Day of February, 2000

Attest:

Q. TODD DICKINSON

Attesting Officer

Acting Commissioner of Patents and Trademarks